US010297012B2

(12) United States Patent
Futamura et al.

(10) Patent No.: US 10,297,012 B2
(45) Date of Patent: May 21, 2019

(54) DYNAMIC ANALYSIS DEVICE, DYNAMIC ANALYSIS SYSTEM, DYNAMIC ANALYSIS METHOD AND NON-TRANSITORY COMPUTER READABLE STORAGE MEDIUM

(71) Applicant: Konica Minolta, Inc., Tokyo (JP)

(72) Inventors: Hitoshi Futamura, Hachioji (JP); Koichi Fujiwara, Osaka (JP); Sho Noji, Kokubunji (JP); Akinori Tsunomori, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 132 days.

(21) Appl. No.: 15/462,237

(22) Filed: Mar. 17, 2017

(65) Prior Publication Data

US 2017/0287114 A1 Oct. 5, 2017

(30) Foreign Application Priority Data

Mar. 30, 2016 (JP) .................................. 2016-067147

(51) Int. Cl.
| | |
|---|---|
| *G06T 5/00* | (2006.01) |
| *G06K 9/46* | (2006.01) |
| *G06T 7/00* | (2017.01) |
| *G06T 11/20* | (2006.01) |
| *A61B 5/00* | (2006.01) |
| *A61B 6/00* | (2006.01) |
| *G06K 9/00* | (2006.01) |
| *A61B 5/024* | (2006.01) |
| *A61B 5/113* | (2006.01) |

(52) U.S. Cl.
CPC ............ *G06T 5/002* (2013.01); *A61B 5/7285* (2013.01); *A61B 6/541* (2013.01); *G06K 9/00771* (2013.01); *G06K 9/4604* (2013.01); *G06T 7/00* (2013.01); *G06T 7/0012* (2013.01); *G06T 7/0016* (2013.01); *G06T 11/206* (2013.01); *A61B 5/024* (2013.01); *A61B 5/113* (2013.01); *G06K 2209/051* (2013.01); *G06T 2207/10016* (2013.01); *G06T 2207/10116* (2013.01); *G06T 2207/30048* (2013.01); *G06T 2207/30061* (2013.01)

(58) Field of Classification Search
CPC ....... G06T 7/00; G06T 7/0012; G06T 7/0016; G06T 11/206; G06T 2207/10116; G06T 2207/30061; G06T 2207/30048; G06T 5/002; A61B 5/024; A61B 5/113; A61B 5/7285; A61B 6/541; G06K 9/4604; G06K 9/00771; G06K 2209/051
USPC ......................................... 382/128, 132, 260
See application file for complete search history.

(56) References Cited

U.S. PATENT DOCUMENTS

| 9,326,745 B2 * | 5/2016 | Muraoka .............. A61B 6/4233 |
| 2016/0098836 A1 * | 4/2016 | Yamato .................... A61B 6/50 |
| | | 382/128 |

FOREIGN PATENT DOCUMENTS

| JP | 5093727 B2 | 9/2012 |
| JP | 2014128687 A | 7/2014 |

* cited by examiner

*Primary Examiner* — Daniel G Mariam
(74) *Attorney, Agent, or Firm* — Lucas & Mercanti, LLP

(57) ABSTRACT

A dynamic analysis device includes a processor. The processor performs filtering on a dynamic image in a feature quantity space formed of two or more axes with feature quantities of the respective axes. The dynamic image is obtained by dynamic imaging performed by emitting radiation to an examination target site. Further, the processor calculates a feature quantity relating to a dynamic state of the examination target site based on the filtered dynamic image.

22 Claims, 13 Drawing Sheets

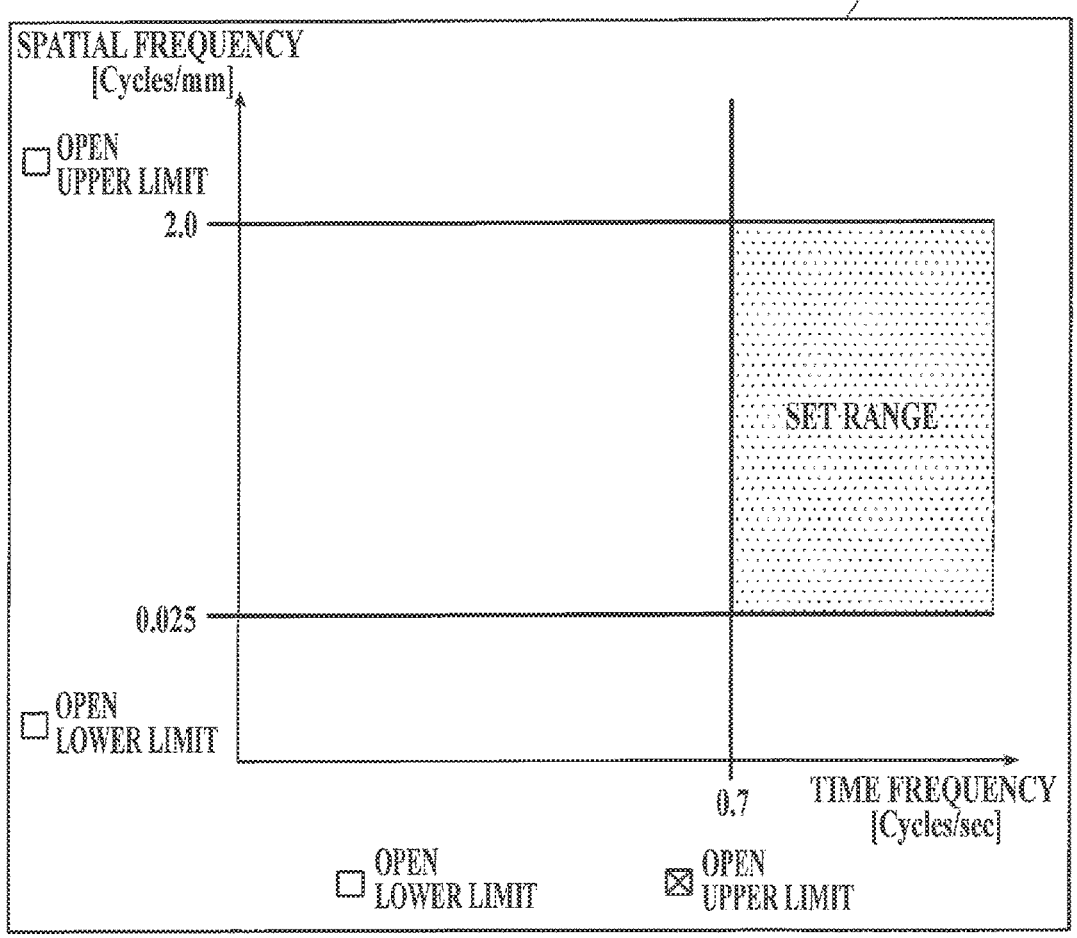

FIG. 12

| SELECT | SEX | AGE | INTRACTABLE DISEASE | RECOMMENDED PARAMETER (FOR BLOOD FLOW ANALYSIS) | | | | RECOMMENDED PARAMETER (FOR VENTILATION ANALYSIS) | | | |
|---|---|---|---|---|---|---|---|---|---|---|---|
| | | | | TIME FREQUENCY | | SPATIAL FREQUENCY | | TIME FREQUENCY | | SPATIAL FREQUENCY | |
| | | | | L | H | L | H | L | H | L | H |
| | M/F | INFANT | | 1.0 | — | 0.05 | 4.0 | 0.5 | 1.0 | 0.1 | 2.0 |
| | M | 10s | | 0.9 | — | 0.05 | 4.0 | 0.4 | 0.9 | 0.1 | 2.0 |
| | M | 20s–30s | | 0.8 | — | 0.025 | 2.0 | 0.4 | 0.8 | 0.05 | 1.0 |
| ✓ | M | 40s–50s | | 0.8 | — | 0.025 | 2.0 | 0.4 | 0.8 | 0.05 | 1.0 |
| | M | 60s AND OVER | | 0.7 | — | 0.025 | 2.0 | 0.3 | 0.7 | 0.05 | 1.0 |

FIG. 13

| NUMBER OF SELECTED TIMES | kV | CURRENT | IMAGING DEVICE | GRID | SET PARAMETER (FOR BLOOD FLOW ANALYSIS) | | | | SET PARAMETER (FOR VENTILATION ANALYSIS) | | | |
|---|---|---|---|---|---|---|---|---|---|---|---|---|
| | | | | | TIME FREQUENCY | | SPATIAL FREQUENCY | | TIME FREQUENCY | | SPATIAL FREQUENCY | |
| | | | | | L | H | L | H | L | H | L | H |
| 520 | 110 | 80mA, 6.3msec, 7.5fps | EXCLUSIVE | 40 LINES / 6:1 | 0.8 | — | 0.025 | 2.0 | 0.4 | 0.8 | 0.05 | 1.0 |
| 231 | 110 | 80mA, 6.3msec, 7.5fps | EXCLUSIVE | 40 LINES / 8:1 | 0.75 | — | 0.025 | 2.0 | 0.4 | 0.8 | 0.05 | 1.0 |
| 394 | 80 | 80mA, 6.3msec, 3.75fps | PORTABLE | 40 LINES / 3:1 | 0.7 | — | 0.025 | 2.0 | 0.3 | 0.7 | 0.05 | 1.0 |
| 249 | 120 | 80mA, 6.3msec, 7.5fps | EXCLUSIVE | 40 LINES / 6:1 | 0.8 | — | 0.025 | 2.0 | 0.4 | 0.8 | 0.05 | 1.0 |

DYNAMIC ANALYSIS DEVICE, DYNAMIC ANALYSIS SYSTEM, DYNAMIC ANALYSIS METHOD AND NON-TRANSITORY COMPUTER READABLE STORAGE MEDIUM

CROSS-REFERENCE TO RELATED APPLICATIONS

This application is based upon and claims the benefit of priority under the Paris Convention of Japanese Patent Application No. 2016-067147 filed on Mar. 30, 2016, the entire disclosure of which, including the specification, claims, drawings and abstract, is incorporated herein by reference in its entirety.

BACKGROUND OF THE INVENTION

1. Field of the Invention

The present invention relates to a dynamic analysis device, a dynamic analysis system, a dynamic analysis method and a non-transitory computer readable storage medium.

2. Description of the Related Art

There have been attempts to utilize, for diagnosis, dynamic images of examination target sites taken with semiconductor image sensors, such as FPDs (Flat Panel Detector), instead of radiation (X-ray) still images of the examination target sites taken with films/screens or photostimulable phosphor plates. More specifically, by making use of high responsivity of semiconductor image sensors in reading/deleting image data, a dynamic state of an examination target site is imaged (photographed) by continuously emitting pulsed radiation from a radiation source in sync with timing of image reading/deletion of a semiconductor image sensor and performing imaging multiple times per second. A series of images obtained by such imaging are displayed in order, so that doctors can observe a series of motions of the examination target site.

By the way, in diagnosis of the lungs, it is important to observe if any part of the lungs functionally (e.g., in ventilation function, pulmonary blood flow function, etc.) decreases. Measurement of the ventilation function with a spirometer and measurement of the pulmonary blood flow function by blood gas analysis are valued as relatively easy-to-use methods. However, local information cannot be known from these, and also which part of the lungs functionally decreases cannot be caught. Meanwhile, for local analysis, measurement of the ventilation function by lung ventilation scintigraphy and measurement of the pulmonary blood flow function by lung perfusion scintigraphy can be used. However, they require inhalation or vascular infusion of radioactive substances, which is a great burden on examinees.

Then, there is a technique for replacing the above examinations by dynamic imaging using the above-described semiconductor image sensor and analysis of data obtained by the imaging.

For example, there is described in Patent Document 1 (Japanese Patent No. 5093727) a technique of, by making use of characteristics of, i.e., change in, pixel value in lung regions of a chest dynamic image taken during breath holding by heartbeat, taking information on the change in pixel value as information on pulmonary blood flow, and making efficient use thereof for diagnosis of pulmonary embolism, heart disease, and so forth.

Further, there is described in Patent Document 2 (Japanese Patent Application Publication No. 2014-128687) a technique of dividing the lung field region of frame images of a chest dynamic image taken during breathing into divisional regions, and performing filtering with a high-pass filter in time direction on time change in pixel signal value in each divisional region, thereby generating a feature quantity relating to pulmonary blood flow in each divisional region.

In dynamic imaging, if the examinee is an able-bodied person, imaging while the examinee is holding his/her breath is relatively easy. However, in medical settings, a situation where imaging while the examinee is holding his/her breath is difficult is often seen; for example, the examinee is an emergency outpatient, a patient undergoing surgery, an infant or an aged person. Hence, the high-accuracy analysis method only if images are taken during breath holding, which is described in Patent Document 1, etc., is not practical in medical settings.

Meanwhile, dynamic images taken during breathing have more analysis-unnecessary signals (noise) than those taken during breath holding, and therefore it is necessary to separate such signals from the rest with high accuracy. For example, in Patent Document 2, filtering with a high-pass filter in the time direction having a cutoff frequency of a fixed value is performed on time change in pixel signal, thereby separating a blood flow signal component from the other signal components. However, filtering with a single feature quantity of a fixed value as a parameter occasionally prevents high-accuracy noise removal due to various factors which include individual difference among examinees.

BRIEF SUMMARY OF THE INVENTION

Objects of the present invention include improving accuracy of noise removal in dynamic images.

In order to achieve at least one of the objects, according to a first aspect of the present invention, there is provided a dynamic analysis device including a processor which: performs filtering on a dynamic image in a feature quantity space formed of two or more axes with feature quantities of the respective axes, the dynamic image being obtained by dynamic imaging performed by emitting radiation to an examination target site; and calculates a feature quantity relating to a dynamic state of the examination target site based on the filtered dynamic image.

According to a second aspect of the present invention, there is provided a dynamic analysis device including a processor which: performs first filtering on a dynamic image with a feature quantity relating to spatial change in pixel signal value of the dynamic image, the dynamic image being obtained by dynamic imaging performed by emitting radiation to an examination target site; performs second filtering on the dynamic image with a feature quantity relating to time change in the pixel signal value of the dynamic image; and calculates a feature quantity relating to a dynamic state of the examination target site based on the first-filtered and second-filtered dynamic image.

According to a third aspect of the present invention, there is provided a dynamic analysis system including: an imaging device which performs dynamic imaging by emitting radiation to an examination target site, thereby obtaining a dynamic image; and the dynamic analysis device.

According to a fourth aspect of the present invention, there is provided a dynamic analysis method including:

performing filtering on a dynamic image in a feature quantity space formed of two or more axes with feature quantities of the respective axes, the dynamic image being obtained by dynamic imaging performed by emitting radiation to an examination target site; and calculating a feature quantity relating to a dynamic state of the examination target site based on the filtered dynamic image.

According to a fifth aspect of the present invention, there is provided a non-transitory computer readable storage medium storing a program for a computer to perform: performing filtering on a dynamic image in a feature quantity space formed of two or more axes with feature quantities of the respective axes, the dynamic image being obtained by dynamic imaging performed by emitting radiation to an examination target site; and calculating a feature quantity relating to a dynamic state of the examination target site based on the filtered dynamic image.

BRIEF DESCRIPTION OF THE SEVERAL VIEWS OF THE DRAWING

The present invention is fully understood from the detailed description given hereinafter and the accompanying drawings, which are given byway of illustration only and thus are not intended to limit the present invention, wherein:

FIG. 9 shows an example of an input window to set filtering parameters;

FIG. 10 shows another example of the input window to set filtering parameters;

FIG. 12 shows another example of the input window to set filtering parameters with a table displayed, the table storing therein examinee background information correlated with recommended parameters for feature quantities;

FIG. 13 shows another example of the input window to set filtering parameters with a table displayed, the table storing therein imaging conditions correlated with filtering parameters set in the past on feature quantities;

DETAILED DESCRIPTION OF THE INVENTION

Hereinafter, an embodiment(s) of the present invention are described in detail with reference to the drawings. However, the scope of the present invention is not limited to the embodiment(s) or illustrated examples.

[Configuration of Dynamic Analysis System 100]

First, the configuration of a dynamic analysis system 100 is described.

Figure 1:
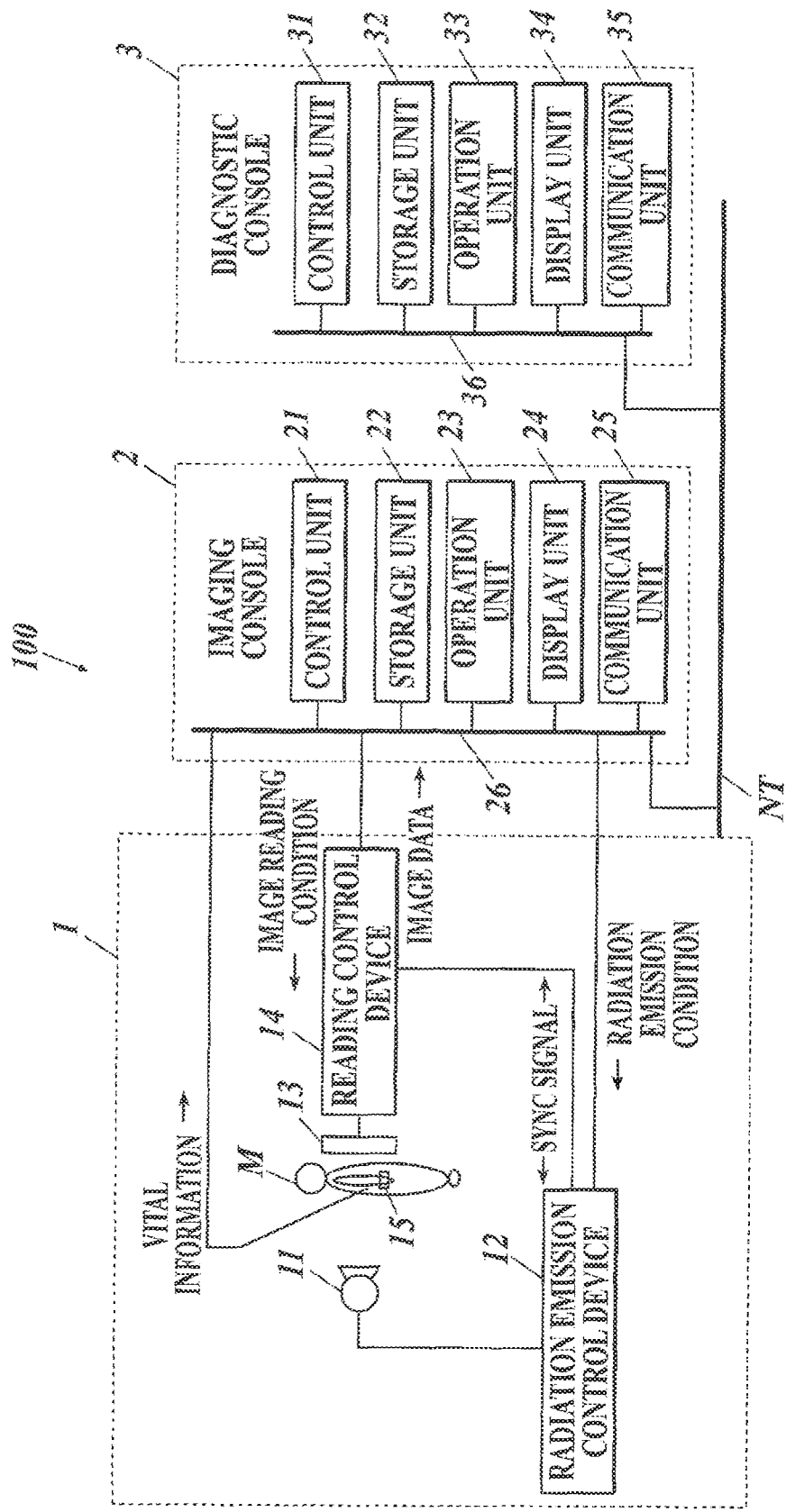
FIG. 1 shows the overall configuration of a dynamic analysis system according to an embodiment(s) of the present invention.

FIG. 1 shows the overall configuration of the dynamic analysis system 100 according to an embodiment(s) of the present invention.

As shown in FIG. 1, the dynamic analysis system 100 includes: an imaging device 1; an imaging console 2 connected with the imaging device 1 via a communication cable or the like; and a diagnostic console 3 connected with the imaging console 2 via a communication network NT, such as a LAN (Local Area Network). In this embodiment, the imaging console 2 and the diagnostic console 3 are connected to the communication network NT with cables, but may be connected thereto wirelessly.

[Configuration of Imaging Device 1]

The imaging device 1 is an imaging unit which images a cyclic dynamic state of a human body. Examples of the cyclic dynamic state include: change in shape of the lungs, i.e., expansion and contraction of the lungs, accompanying respiration; and pulsation of the heart. Dynamic imaging is performed by repeatedly emitting pulsed radiation, such as X-rays, to a subject M at predetermined time intervals (pulse emission) or continuously emitting radiation without a break to a subject Mat a low dose rate (continuous emission), thereby obtaining a plurality of images showing the dynamic state. A series of images obtained by dynamic imaging is called a dynamic image. Images constituting a dynamic image are called frame images. In the embodiment(s) described below, dynamic imaging is performed by pulse emission as an example.

A radiation source 11 is disposed to face a radiation detection unit 13 having a subject M in between, and emits radiation (X-rays) to the subject M under the control of a radiation emission control device 12.

The radiation emission control device 12 is connected with the imaging console 2, and controls the radiation source 11 based on radiation emission conditions input from the imaging console 2 so as to perform radiation imaging. The radiation emission conditions input from the imaging console 2 include a pulse rate, a pulse width, a pulse interval, the number of frames (frame images) to be taken by one imaging, a value of current of an X-ray tube, a value of voltage of the X-ray tube, a type of grid, and a type of added filter. The pulse rate is the number of times radiation is emitted per second, and matches the frame rate described below. The pulse width is a period of time for one radiation emission. The pulse interval is a period of time from the start of one radiation emission to the start of the next radiation emission, and matches the frame interval described below.

The radiation detection unit 13 is constituted of a semiconductor image sensor, such as an FPD. The FPD is constituted of detection elements (pixels) arranged at predetermined points on a substrate, such as a glass substrate, in a matrix. The detection elements detect radiation (intensity of radiation) which has been emitted from the radiation source 11 and passed through at least a subject M, convert the detected radiation into electric signals, and accumulate the electric signals therein. The pixels are provided with switching elements, such as TFTs (Thin Film Transistors). There are an indirect conversion type FPD which converts X-rays into electric signals with photoelectric conversion element(s) via scintillator(s) and a direct conversion type FPD which directly converts X-rays into electric signals. Either of them can be used. The radiation detection unit 13 is disposed to face the radiation source 11 having a subject M in between.

In the radiation detection unit 13, signal values of pixels (pixel signal values) of obtained images are values obtained by converting the intensity of the radiation reaching the radiation detection unit 13 into electric signals, namely, values correlating with the intensity of the radiation reaching the radiation detection unit 13. The higher the intensity of the reached radiation is, the higher the pixel signal value is. Meanwhile, in the imaging console 2 and the diagnostic console 3, pixel signal values are treated as those representing absorbed doses, in the embodiment(s) described hereinafter. That is, the imaging console 2 converts pixel signal values of a series of frame images received with the communication unit 25 into values representing absorbed doses, and sends the values to the diagnostic console 3. That is, in the imaging console 2 and the diagnostic console 3, the higher the absorbed dose is, the higher the pixel signal value is, and such a pixel is depicted white (low density) on an image.

A reading control device 14 is connected with the imaging console 2. The reading control device 14 controls the switching elements of the pixels of the radiation detection unit 13 based on the image reading conditions input from the imaging console 2 to switch the pixels to read the electric signals accumulated in the pixels, thereby reading the electric signals accumulated in the radiation detection unit 13 and obtaining image data. This image data is a frame image(s). The reading control device 14 outputs the obtained frame images to the imaging console 2. The image reading conditions include a frame rate, a frame interval, a pixel size and an image size (matrix size). The frame rate is the number of frame images obtained per second, and matches the pulse rate described above. The frame interval is a period of time from the start of one frame image obtaining action to the start of the next frame image obtaining action, and matches the pulse interval described above.

The radiation emission control device 12 and the reading control device 14 are connected with one another, and exchange sync signals with one another so as to synchronize radiation emission actions with image reading actions.

In the state of being in sync with dynamic imaging, a vital sensor 15 obtains vital information on the dynamic state of an examination target site, and outputs the obtained vital information to the imaging console 2. The vital sensor 15 is, for example, a pulse oximeter.

[Configuration of Imaging Console 2]

The imaging console 2 outputs the radiation emission conditions and the image reading conditions to the imaging device 1 so as to control radiation imaging and the radiation image reading actions performed by the imaging device 1, and also displays the dynamic image(s) obtained by the imaging device 1 so that a radiographer, such as a radiologist, can check if performed positioning has no problem, and can determine if the image is suitable for diagnosis.

The imaging console 2 includes, as shown in FIG. 1, a control unit 21, a storage unit 22, an operation unit 23, a display unit 24 and a communication unit 25. These units are connected to one another via a bus 26.

The control unit 21 includes a CPU (Central Processing Unit) and a RAM (Random. Access Memory). The CPU of the control unit 21 reads a system program and various process programs stored in the storage unit 22 in response to operations through the operation unit 23, opens the read programs in the RAM, and performs various processes, such as the below-described imaging control process, in accordance with the opened programs, thereby performing concentrated control of actions of the units or the like of the imaging console 2 and the radiation emitting actions and the reading actions of the imaging device 1.

The storage unit 22 is constituted of a nonvolatile semiconductor memory, a hard disk or the like. The storage unit 22 stores therein various programs to be executed by the control unit 21, parameters necessary to perform processes of the programs, data, such as process results, and so forth. For example, the storage unit 22 stores therein a program for the imaging control process shown in FIG. 2. The storage unit 22 also stores therein the radiation emission conditions and the image reading conditions correlated with examination target sites (here, the chest) and types of analysis target. The programs are stored in the form of a computer readable program code(s), and the control unit 21 performs actions in accordance with the program code.

The operation unit 23 includes: a keyboard including cursor keys, number input keys and various function keys; and a pointing device, such as a mouse, and outputs, to the control unit 21, command signals input by key operation on the keyboard or by mouse operation. The operation unit 23 may have a touch panel on a display screen of the display unit 24. In this case, the operation unit 23 outputs command signals input via the touch panel to the control unit 21.

The display unit 24 is constituted of a monitor, such as an LCD (Liquid Crystal Display) or a CRT (Cathode Ray Tube), and displays thereon commands input from the operation unit 23, data and so forth in accordance with commands of display signals input from the control unit 21.

The communication unit 25 includes a LAN adapter, a modem and a TA (Terminal Adapter), and controls data exchange with devices connected to the communication network NT.

[Configuration of Diagnostic Console 3]

The diagnostic control 3 is a dynamic analysis device which obtains the dynamic image(s) from the imaging console 2, analyzes the obtained dynamic image, and displays the analysis result to help a doctor(s) make a diagnosis.

The diagnostic console 3 includes, as shown in FIG. 1, a control unit 31, a storage unit 32, an operation unit 33, a display unit 34 and a communication unit 35. These units are connected to one another via a bus 36.

The control unit 31 includes a CPU and a RAM. The CPU of the control unit 31 reads a system program and various process programs stored in the storage unit 32 in response to operations through the operation unit 33, opens the read programs in the RAM, and performs various processes, such as the below-described image analysis process, in accordance with the opened programs, thereby performing concentrated control of actions of the units or the like of the diagnostic console 3.

The storage unit 32 is constituted of a nonvolatile semiconductor memory, a hard disk or the like. The storage unit 32 stores therein various programs, including a program for the image analysis process, to be executed by the control unit 31, parameters necessary to perform processes of the programs, data, such as process results, and so forth. The programs are stored in the form of a computer readable program code(s), and the control unit 31 performs actions in accordance with the program code.

The storage unit 32 also stores therein values of parameters used in filtering (called "filtering parameters") for noise removal in the below-described image analysis process, values of recommended parameters for respective examinee background information, such as sexes and ages.

The operation unit 33 includes: a keyboard including cursor keys, number input keys and various function keys; and a pointing device, such as a mouse, and outputs, to the control unit 31, command signals input by key operation on the keyboard or by mouse operation. The operation unit 33 may have a touch panel on a display screen of the display unit 34. In this case, the operation unit 33 outputs command signals input via the touch panel to the control unit 31.

The display unit 34 is constituted of a monitor, such as an LCD or a CRT, and performs various types of display in accordance with commands of display signals input from the control unit 31.

The communication unit 35 includes a LAN adapter, a modem and a TA, and controls data exchange with devices connected to the communication network NT.

[Actions of Dynamic Analysis System 100]

Next, actions of the dynamic analysis system 100 are described.

(Actions of Imaging Device 1 and Imaging Console 2)

First, imaging actions performed by the imaging device 1 and the imaging console 2 are described.

Figure 2:
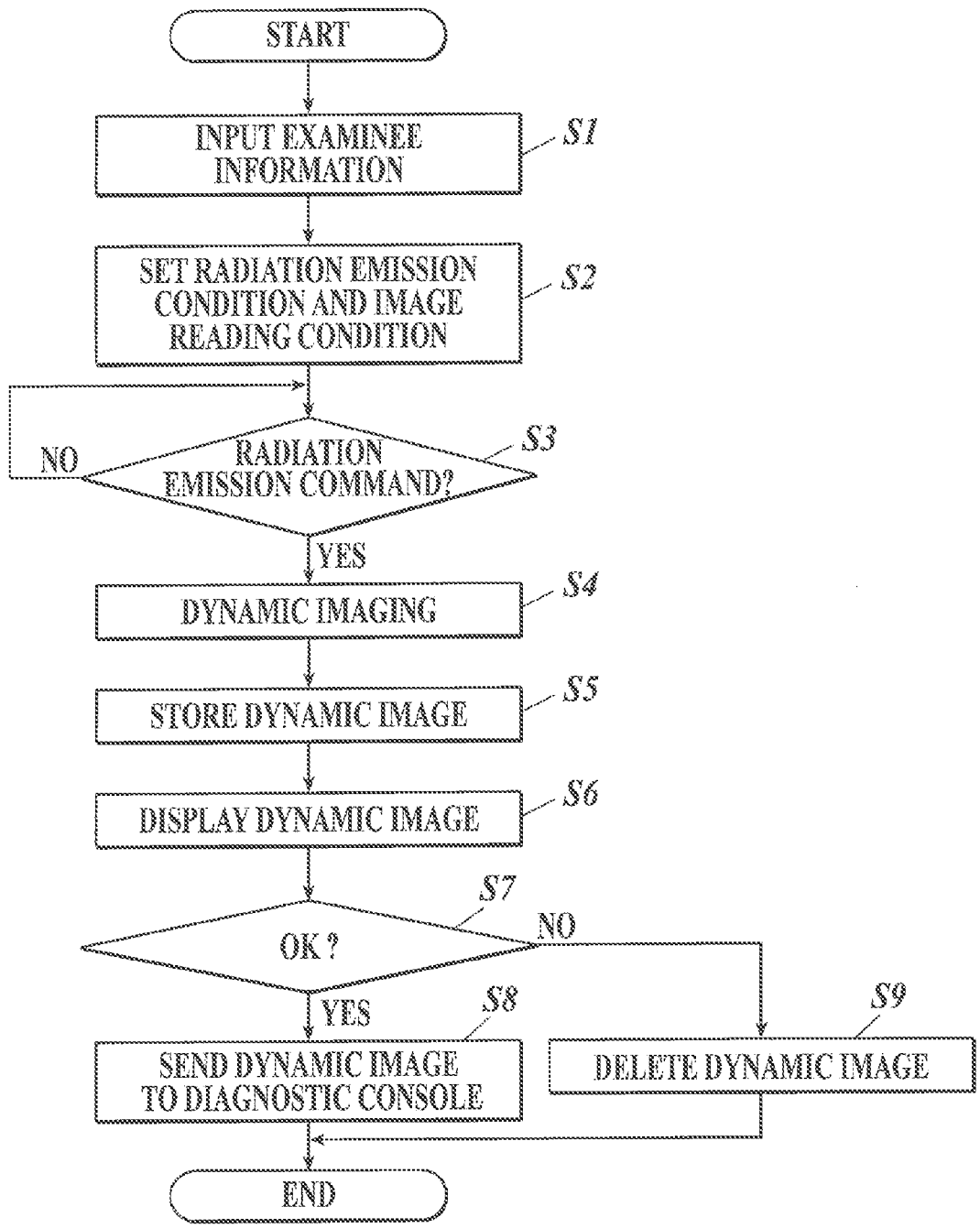
FIG. 2 is a flowchart showing an imaging control process performed by a control unit of an imaging console shown in FIG. 1.

FIG. 2 shows the imaging control process performed by the control unit 21 of the imaging console 2. The imaging control process is performed by the control unit 21 in cooperation with the program stored in the storage unit 22.

First, a radiographer operates the operation unit 23 of the imaging console 2 so as to input information on an examinee, who is a subject M, (called "examinee information" e.g., examinee ID, examinee name, and examinee background information (examinee physical features, such as height, weight, age and sex)), and examination information (examination target site (here, the chest), type of analysis target (ventilation, pulmonary blood flow, etc.), etc.) (Step S1). The examinee information and/or the examination information may be received from an RIS (Radiology Information System) through the communication unit 25.

Next, based on the input examination information, the control unit 21 reads the radiation emission conditions from the storage unit 22 so as to set them in the radiation emission control device 12, and also reads the image reading conditions from the storage unit 22 so as to set them in the reading control device 14 (Step S2). The radiation emission conditions and the image reading conditions can be adjusted by radiographer operation on the operation unit 23, and the adjusted conditions can be set.

Next, the control unit 21 waits for a radiation emission command to be input by radiographer operation on the operation unit 23 (Step S3). Here, if imaging to be performed is imaging during breathing, the radiographer instructs the examinee (subject M) to relax and encourages him/her to do quiet breathing. When preparations for imaging are complete, the radiographer operates the operation unit 23 so as to input a radiation emission command.

When receiving the radiation emission command input through the operation unit 23 (Step S3; YES), the control unit 21 outputs an imaging start command to the radiation emission control device 12 and the reading control device 14 to start dynamic imaging (Step S4). That is, the radiation source 11 emits radiation at pulse intervals set in the radiation emission control device 12, and accordingly the radiation detection unit 13 obtains (generates) a series of frame images.

When imaging for a predetermined number of frame images finishes, the control unit 21 outputs an imaging end command to the radiation emission control device 12 and the reading control device 14 to stop the imaging actions. The number of frame images to be taken covers at least one respiration cycle.

Each time a frame image is obtained by imaging, the obtained frame image is input to the imaging console 2 and stored in the storage unit 22, the frame image being correlated with a number indicating what number in the imaging order the frame image has been taken (frame number) (Step S5), and also is displayed on the display unit 24 (Step S6). The radiographer checks the positioning or the like with the displayed dynamic image, and determines whether the dynamic image obtained by dynamic imaging is suitable for diagnosis (Imaging OK) or re-imaging is necessary (Imaging NG). Then, the radiographer operates the operation unit 23 so as to input the determination result.

When the determination result "Imaging OK" is input by radiographer operation on the operation unit 23 (Step S7; YES), the control unit 21 attaches, to the frame images obtained by dynamic imaging (e.g., writes, in the header region of the image data), supplementary information such as an ID to identify the dynamic image, the examinee information, the examination information, the radiation emission conditions, the image reading conditions, and the respective numbers indicating what number in the imaging order the respective frame images have been taken (frame numbers), and sends the same to the diagnostic console 3 through the communication unit 25 (Step S8), and then ends the imaging control process. On the other hand, when the determination result "Imaging NG" is input by radiographer operation on the operation unit 23 (Step S7; NO), the control unit 21 deletes the frame images from the storage unit 22 (Step S9), and then ends the imaging control process. In this case, re-imaging is necessary.

(Actions of Diagnostic Console 3)

Next, actions of the diagnostic console 3 are described.

Figure 3:
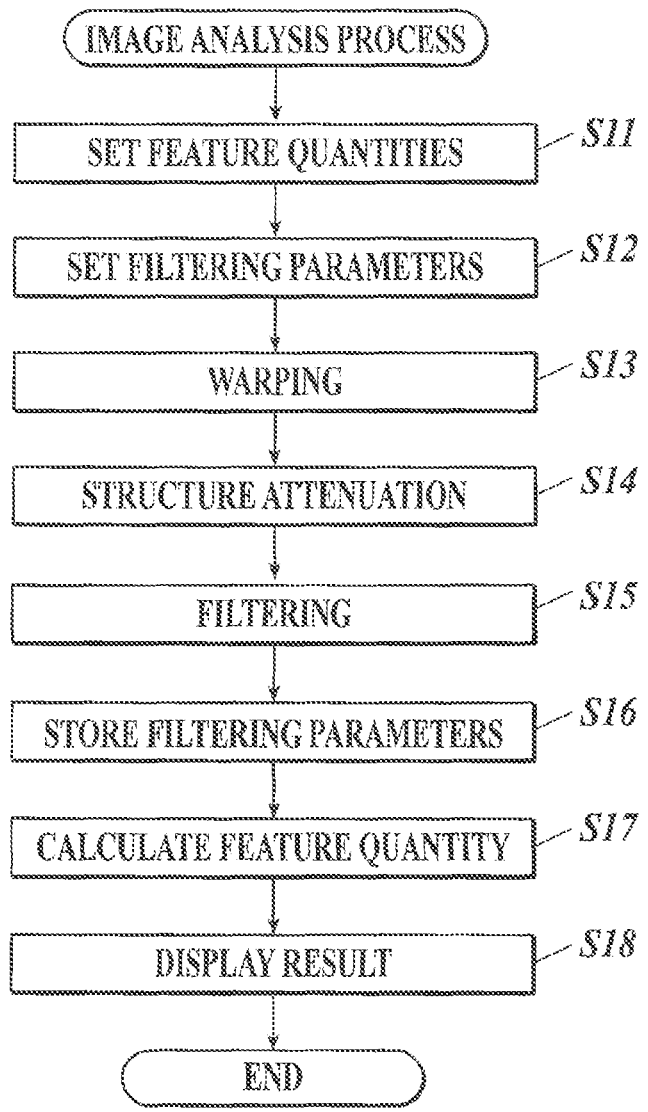
FIG. 3 is a flowchart showing an image analysis process performed by a control unit of a diagnostic console shown in FIG. 1.

In the diagnostic console 3, when receiving a series of frame images of a dynamic image from the imaging console 2 through the communication unit 35, the control unit 31 performs the image analysis process shown in FIG. 3 in cooperation with the program stored in the storage unit 32.

Hereinafter, the flow of the image analysis process is described with reference to FIG. 3.

First, the control unit 31 sets feature quantities to be used in filtering for noise removal (Step S11).

According to the studies of the inventors of this application, et al., signal components contained in a dynamic image can be classified on a feature quantity space formed of two or more axes having mutually different characteristics, such as a feature quantity space formed of two or more axes including an axis representing a feature quantity relating to time change in pixel signal value of a dynamic image and an axis representing a feature quantity relating to spatial change in pixel signal value of the dynamic image. The "having mutually different characteristics" means that feature quantities of the axes do not depend on one another, including feature quantities being the same. The "depend" means, for example, as "y=3x", determination of a value of one variable determines a value of the other variable. The axes representing the same item (e.g., two axes both representing spatial frequency) and the axes representing substantially the same item (e.g., axes respectively representing radius and area) are excluded from the above-described "two or more axes having mutually different characteristics".

Figure 4:
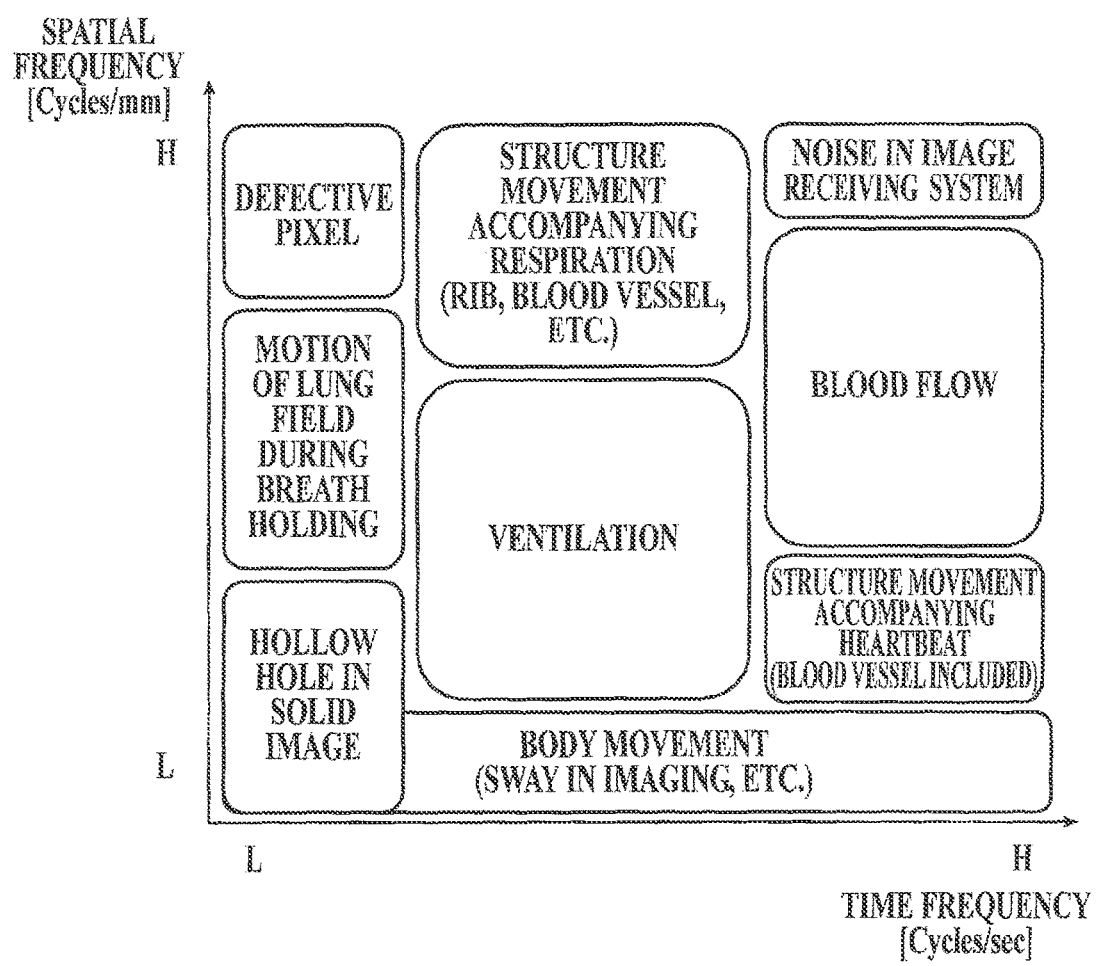
FIG. 4 shows the result of classification of signal components which can be contained in dynamic images of the chest on a graph of a feature quantity space formed of two axes, wherein the horizontal axis represents time frequency of pixel signal values of the dynamic images, and the vertical axis represents spatial frequency of the pixel signal values of the dynamic images.

FIG. 4 shows the result of classification of signal components which can be contained in dynamic images of the chest on a graph of a feature quantity space formed of two axes, wherein the horizontal axis represents frequency of time change in pixel signal value of the dynamic images (hereinafter called "time frequency"), and the vertical axis represents frequency of spatial change in pixel signal value of the dynamic images (hereinafter called "spatial frequency"). That is, signal components which are not desired to be extracted (i.e., noise) can be removed with high accuracy by (i) setting, for a signal component which is desired to be extracted, an upper limit(s) and/or a lower limit(s) as a filtering parameter(s) on feature quantities of a feature quantity space formed of two or more axes having mutually different characteristics, and (ii) performing filtering.

Figure 5:
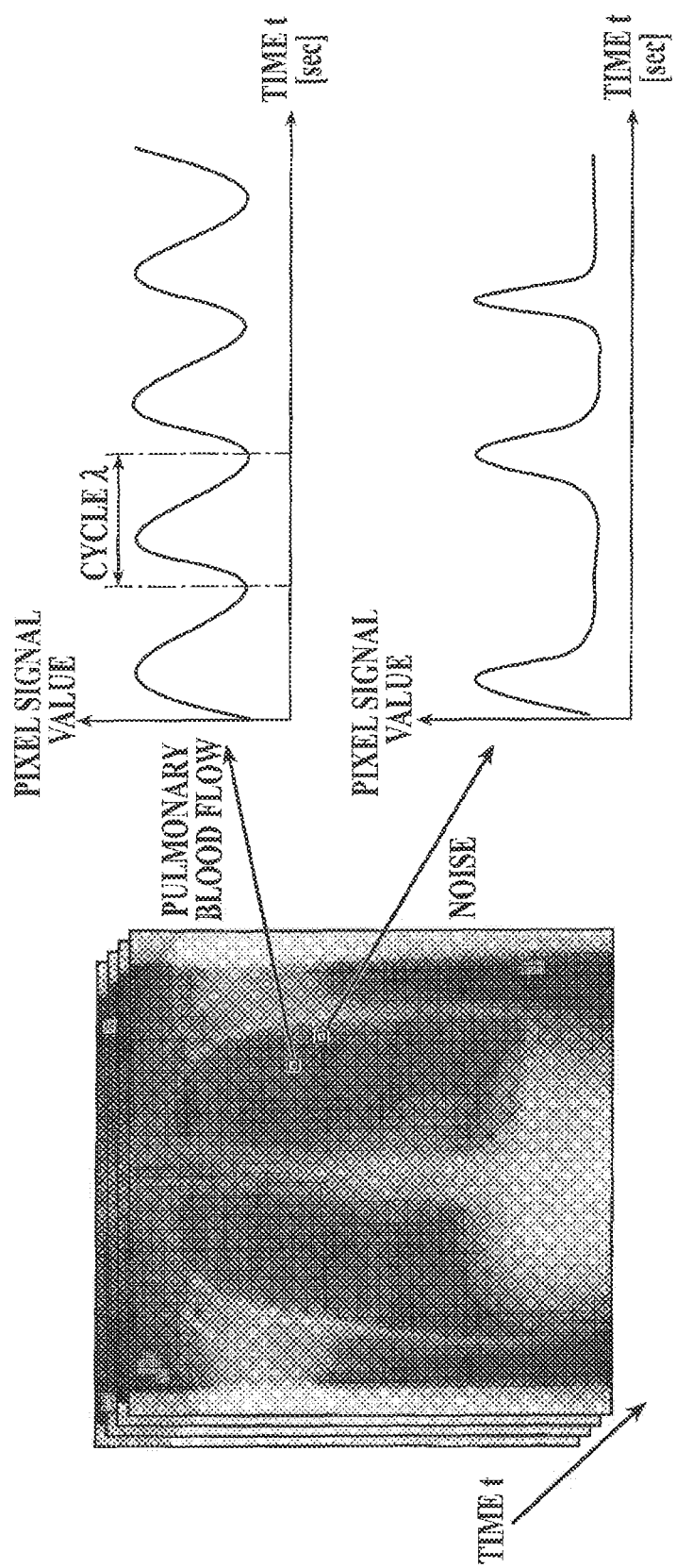
FIG. 5 shows time change in pixel signal value accompanying pulmonary blood flow and time change in pixel signal value accompanying noise.

Examples of the feature quantity relating to time change in pixel signal value of a dynamic image include: the above-described time frequency (frequency of waveform formed by plotting pixel signal values on the vertical axis against elapsed time from start of dynamic imaging on the horizontal axis); and a feature quantity relating to a profile shape of pixel signal values of a dynamic image in the time direction (shape of the above-described waveform). In heartbeat, systole is shorter than diastole, and as shown in FIG. 5, time change in pixel signal value accompanying pulmonary blood flow shows asymmetrical peaks as if one "ascends a steep slope and descends a gentle slope". Meanwhile, time change in pixel signal value of a noise component does not show such behavior as shown in FIG. 5. Hence, if it is desired to extract a signal component of pulmonary blood flow (blood flow signal component), a feature quantity representing asymmetry of peaks in a profile shape of pixel signal values of a dynamic image in the time direction can be a feature quantity to be used in filtering.

Examples of the feature quantity representing asymmetry of peaks in a profile shape of pixel signal values of a dynamic image in the time direction include: peak integral; peak distance; a speed ratio; an acceleration ratio; skewness; and a value representing a degree of likeness to blood flow (likelihood) output from a machine learning classifier when the above-described profile shape is input to the classifier.

Figure 6:
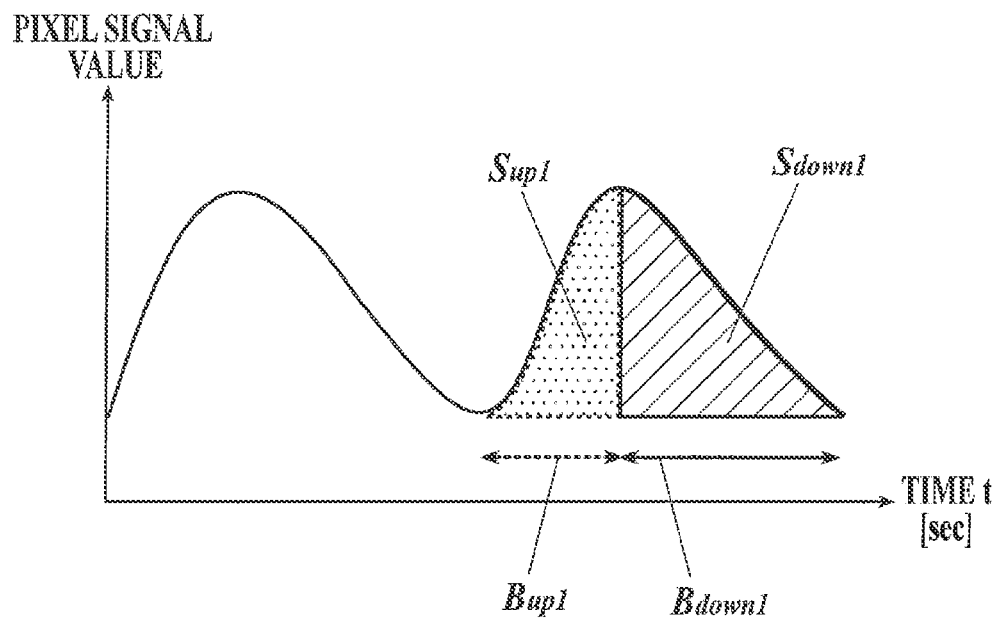
FIG. 6 is an illustration to explain peak integral.

The peak integral is a statistic relating to a signal integral value $Sup$, which is a signal integral value during signal value increase, and a signal integral value $Sdown$, which is a signal integral value during signal value decrease, in each cycle (see FIG. 6), and can be obtained, for example, by any one of the following Formula 1 to Formula 3. In the formulae, j represents a cycle number, MAX represents a maximum value, and MED represents a median. These apply to Formula 4 to Formula 12 too.

$\Sigma Sdown_j / \Sigma Sup_j$ (Formula 1)

$MAX(Sdown_j)/MAX(Sup_j)$ (Formula 2)

$MED(Sdown_j)/MED(Sup)$ (Formula 3)

The peak distance is a statistic relating to rising time $Bup$, which is a period of time of signal value increase, and falling time $Bdown$, which is a period of time of signal value decrease, in each cycle (see FIG. 6), and can be obtained, for example, by any one of the following Formula 4 to Formula 6.

$\Sigma Bdown_j / \Sigma Bup_j$ (Formula 4)

$MAX(Bdown_j)/MAX(Bup_j)$ (Formula 5)

$MED(Bdown_j)/MED(Bup)$ (Formula 6)

Figure 7:
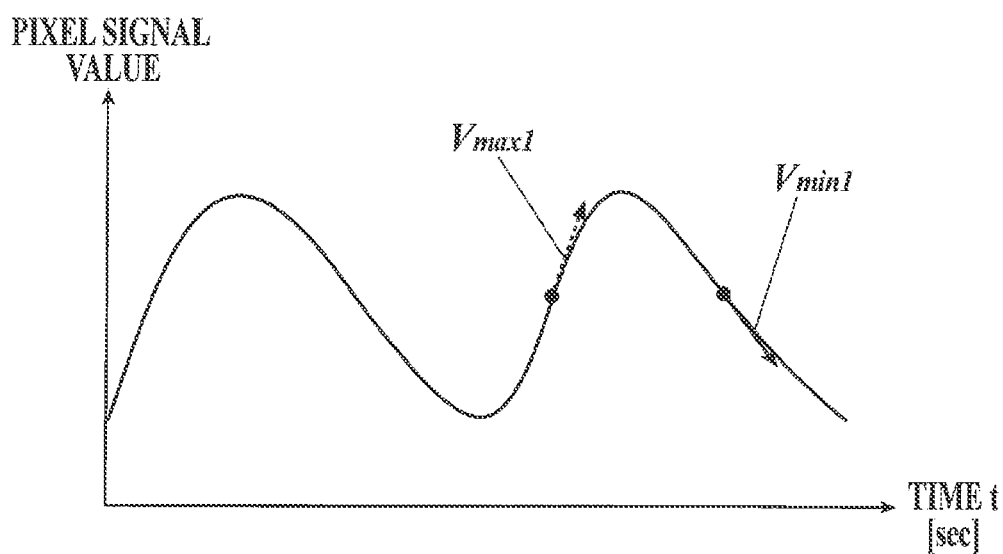
FIG. 7 is an illustration to explain a speed ratio.

The speed ratio is a statistic relating to a maximum value $Vmax$, which is the maximum value of inclination, and a minimum value $Vmin$, which is the minimum value of inclination, in each cycle (see FIG. 7), and can be obtained, for example, by any one of the following Formula 7 to Formula 9. In the formulae, ABS represents an absolute value.

$\Sigma ABS(VMax_j)/\Sigma ABS(Vmin_j)$ (Formula 7)

$MAX(ABS(VMax_j))/MAX(ABS(Vmin_j))$ (Formula 8)

$MED(ABS(VMax_j))/MED(ABS(Vmin_j))$ (Formula 9)

Figure 8:
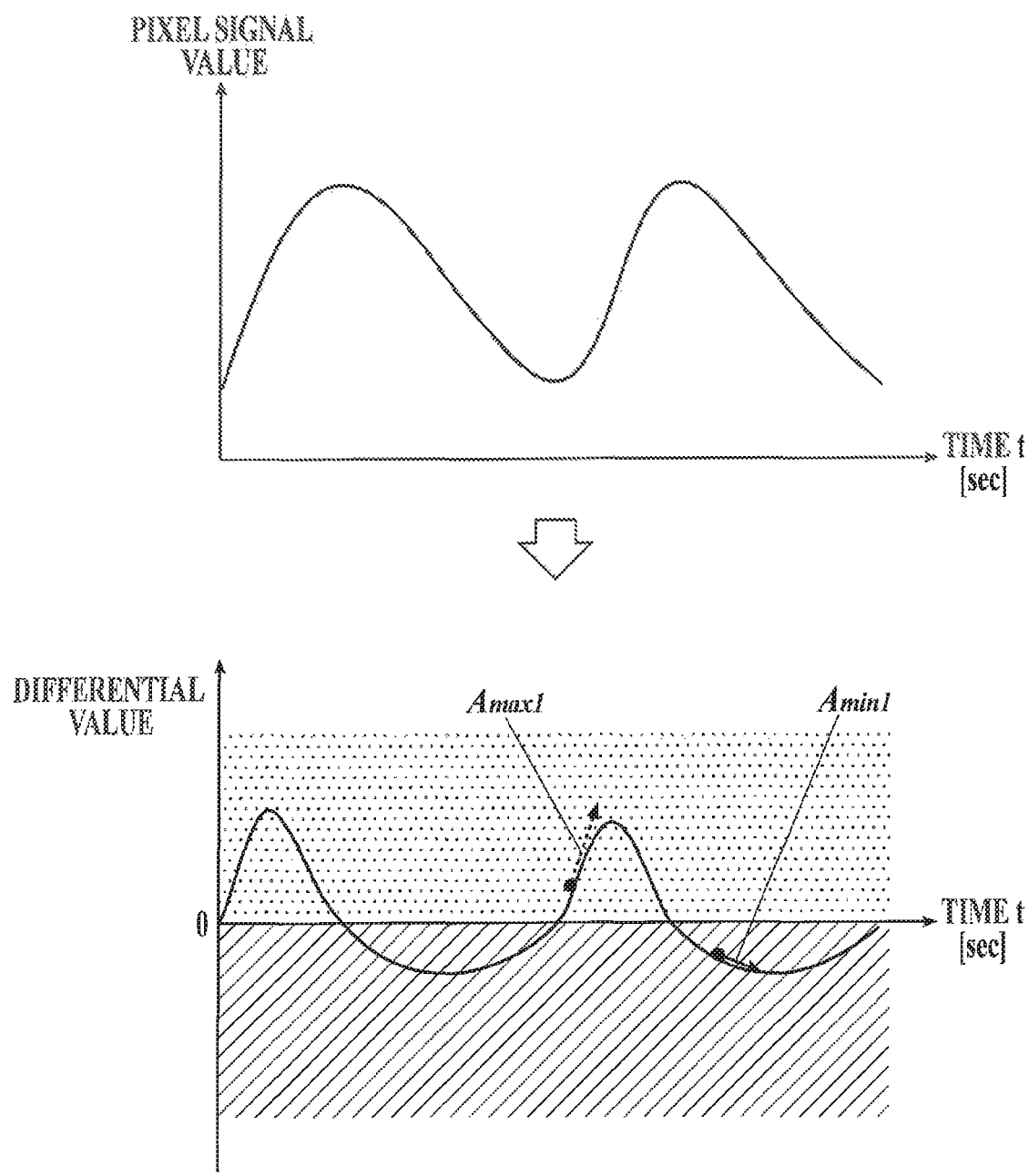
FIG. 8 is an illustration to explain an acceleration ratio.

The acceleration ratio is a statistic relating to, regarding differential values obtained by differentiating pixel signal values in each cycle, a maximum differential value (second derivative of the signal value(s)) $Amax$, which is the maximum differential value in the region of positives (area indicated by dots in FIG. 8), and a minimum differential value (second derivative of the signal value(s)) $Amin$, which is the minimum differential value in the region of negatives (area indicated by oblique lines in FIG. 8), in each cycle, and can be obtained by any one of the following Formula 10 to Formula 12.

$\Sigma ABS(Amax_j)/\Sigma ABS(Amin_j)$ (Formula 10)

$MAX(ABS(Amax_j))/MAX(ABS(Amin_j))$ (Formula 11)

$MED(ABS(Amax_j))/MED(ABS(Amin_j))$ (Formula 12)

The above peak integral, peak distance, speed ratio and acceleration ratio show high values for the blood flow signal component and low values for noise.

As to the skewness, first, skewness of each cycle is calculated by the following Formula 13, and a statistic of calculated (values of) skewness of cycles can be used as the feature quantity relating to time change in pixel signal value of a dynamic image. Examples of the statistic of skewness of cycles include: the maximum value of skewness of cycles; the mean in the top desired percentage of skewness of cycles; and the mode of skewness of cycles. For example, the maximum value is high for the blood flow signal component and low for noise.

[Equation 1]

$$SKEW_j = \frac{\frac{1}{n_j}\sum_{i=j*T}^{(j+1)*T-1}(f(i)-\overline{f}_j)^3}{\left\{\frac{1}{n_j}\sum_{i=j*T}^{(j+1)*T-1}(f(i)-\overline{f}_j)^2\right\}^{3/2}}$$ (Formula 13)

$$\overline{f}_j = \frac{1}{n_j}\sum_{i=j*T}^{(j+1)*T-1}(f(i))$$

In the formula, f(i) represents a pixel signal value, $n_j$ represents the number of samplings per cycle, T represents a cycle, j represents a cycle number, and i represents a sampling index.

The output result output from a machine learning classifier when data showing a profile shape of pixel signal values of a dynamic image in the time direction is input to the classifier can also be used as the feature quantity relating to a profile shape of pixel signal values of a dynamic image in the time direction. For example, likelihood or the like of a blood flow class output when data showing the above-described profile shape is input to deep leaning, DNN (Deep Natural Network) or the like described in Non-Patent Document 1 or 2 can be used (Non-Patent Document 1: Takayuki OKATANI, "Deep Learning and Image Recognition—Basis and Current Trend—", Communications of the Operations Research Society of Japan, Vol. 60 (4), pp. 191-197, 2015, and Non-Patent Document 2: "Deep Learning", complied under the supervision of The Japanese Society for Artificial Intelligence, Kindai Kagaku Sha Co., Ltd., 2015). For example, likelihood of a blood flow class (value representing a degree of likeness to blood flow) output from a convolutional natural network, described in Non-Patent Document 1, when original data (e.g., 25×25 data) obtained by sampling pixel signal values of a region of interest (e.g., 5 pixels×5 pixels) within a specific period of time in a dynamic image a predetermined number of times (e.g., 25 times) is input to the convolutional natural network can be used.

Further, examples of the feature quantity relating to spatial change in pixel signal value of a dynamic image include: the above-described spatial frequency; and a curvature feature quantity. The curvature feature quantity is an indicator indicating degree of curve of a curved line or a curved surface, and can express, in numerical value, a shape in a three-dimensional space obtained by plotting pixel signal values on z axis against x and y axes representing positional coordinates of pixels of an image (i.e., the shape of a curved surface showing distribution of pixel signal values on an image). This shape can be obtained by calculating the curvature feature quantity with respect to the pixel signal value f(x,y) corresponding to coordinates (x,y) of each pixel of an input image, setting a filtering parameter(s) on the curvature feature quantity, and performing filtering.

Examples of the curvature feature quantity include ShapeIndex value SI(x,y) described in Japanese Patent Application Publication No. 2006-230904; and Gaussian curvature and mean curvature described in Japanese Patent Application Publication No. 2005-80758. If ShapeIndex value SI(x,y) is used as the curvature feature quantity, filtering can be performed by the following formulae by automatically setting "less than 0.25" as a filtering parameter(s) on SI(x,y).

If $SI(x,y)<0.25, f(x,y)=f(x,y)$.

If $SI(x,y)≥0.25, f(x,y)=0$.

In Step S11, among the above or other feature quantities, feature quantities of two or more axes having mutually different characteristics are set. The feature quantities can be set by a user through the operation unit 33. If the feature quantities to be used in filtering are predetermined (e.g., only time frequency and spatial frequency are prepared as the feature quantities), Step S11 can be skipped.

Hereinafter, description is made, as an example, about a case where the time frequency and the spatial frequency are set as feature quantities to be used in filtering.

Next, the control unit 31 sets filtering parameters for the respective feature quantities (Step S12). In Step S12, as the filtering parameters, the upper limit(s) and/or the lower limit(s) of a range to extract are set with respect to the respective feature quantities set in Step S11. The filtering parameters may be set manually or automatically.

Hereinafter, examples of setting of the filtering parameters in Step S12 are described.

For example, an input window 341 provided with entry fields of upper limits and lower limits for the feature quantities as shown in FIG. 9 is displayed on the display unit 34, and numerical values input there by user operation on the operation unit 33 are set as the filtering parameters.

Alternatively, an input window 342 where a graph of the feature quantity space formed of the axes representing the respective feature quantities set in Step S11 as shown in FIG. 10 may be displayed on the display unit 34, and when upper limit points and lower limit points for the axes are specified by user operation on the operation unit 33, values corresponding to the specified points are set as the filtering parameters. For example, lines to indicate upper limit points and lower limit points for the axes are displayed on the graph of the feature quantity space, and upper limit points and lower limit points for the axes can be specified by sliding the lines through the operation unit 33. Alternatively, for the respective axes, check boxes to specify "Open Upper Limit" and "Open Lower Limit" may be displayed, and upper limits and lower limits can be open by checking (or ticking) the boxes. In this case, a line corresponding to a limit for which a check box is checked is hidden. For example, as shown in FIG. 10, when the check box "Open Upper Limit" for the time frequency is checked, the line to indicate an upper limit point on the time frequency is hidden.

Figure 11:
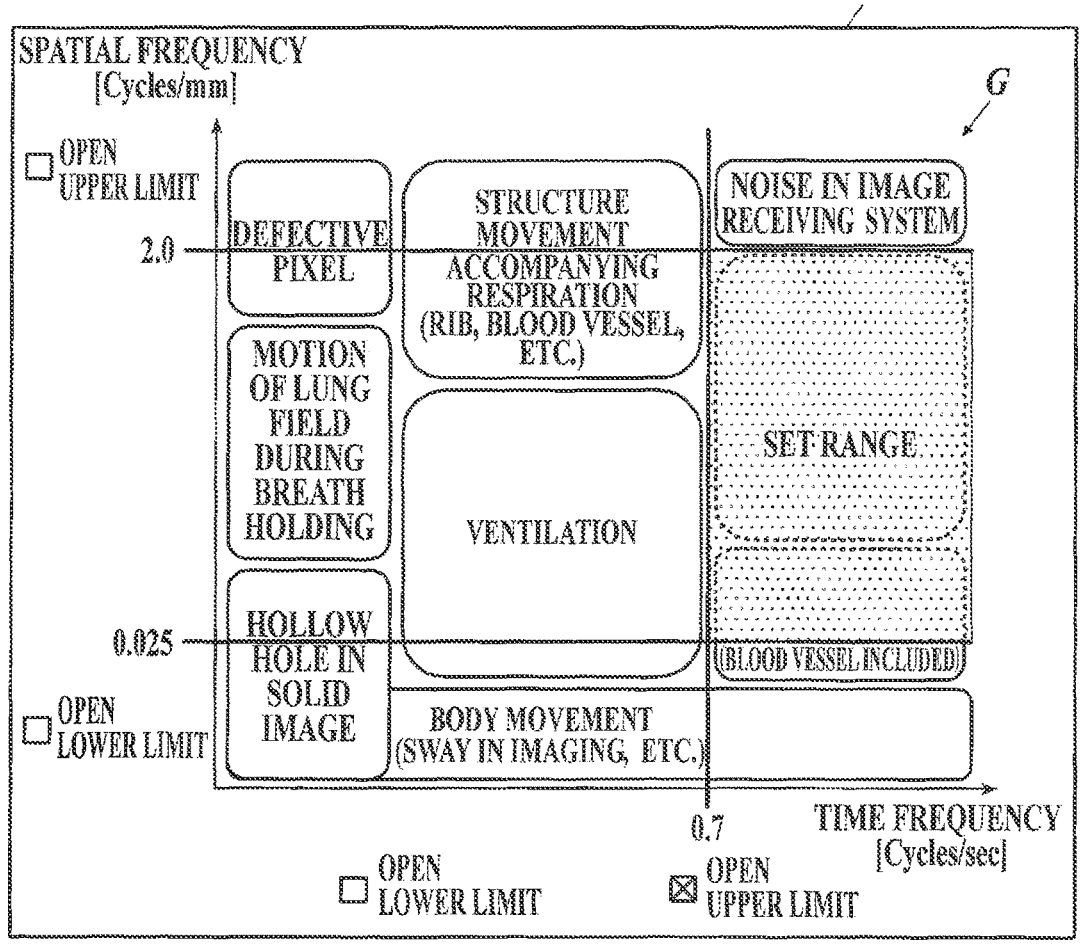
FIG. 11 shows another example of the input window to set filtering parameters with guidance information displayed, the guidance information showing classification of signal components possibly being contained in dynamic images of an examination target site on a graph of a feature quantity space formed of two or more axes.

As shown in FIG. 11, in the input window 342, guidance information G may also be displayed. The guidance information G shows the result of classification of signal components which can be contained in dynamic images of an examination target site on a graph of a feature quantity space formed of two or more axes. This allows a user to intuitively understand meanings of feature quantities and to readily set values of filtering parameters.

In FIG. 9 to FIG. 11, the range set by filtering parameters is one. However, two or more ranges may be set.

Alternatively, the filtering parameters may be set by referring to filtering parameters set in past examinations and stored in the storage unit 32.

For example, filtering parameters set in a past examination(s) on the same examinee (filtering parameters which (i) are correlated and stored in the storage unit 32 with the same examinee ID and the same type of analysis target as those contained in the supplementary information attached to the dynamic image to be filtered, and (ii) are for the feature quantities set in Step S11) are retrieved from the storage unit 32, and the retrieved (values of) filtering parameters are set as this-time filtering parameters (filtering parameters to be used in filtering this time).

Alternatively, the filtering parameters may be set as follows: store in the storage unit 32 in advance a table (correspondence table) in which sexes, ages and so forth, which are of examinee background information, are correlated with filtering parameters recommended for feature quantities (called "recommended parameters"); and set, among recommended parameters correlated with the examinee background information (sex, age, etc.) which corresponds to the examinee background information contained in the supplementary information attached to the dynamic image, values of recommended parameters for the type of analysis target and the feature quantities set in Step S11 as this-time filtering parameters. In this case, for example, as shown in FIG. 12, the correspondence table stored in the storage unit 32 may be displayed on the display unit 34. Then, the filtering parameters are set in response to user operation on the operation unit 33.

Alternatively, the filtering parameters may be set as follows: store in the storage unit 32 in advance a table (correspondence table) in which imaging conditions (radiation emission conditions) are correlated with the actual results (past records) of filtering parameters of feature quantities set for dynamic images taken in the past under the imaging conditions; and set, as this-time filtering parameters, values of filtering parameters which (i) are correlated, in the correspondence table stored in the storage unit 32, with the same imaging conditions as those contained in the supplementary information attached to the dynamic image, and (ii) are for the feature quantities set in Step S11. In this case, for example, as shown in FIG. 13, the correspondence table stored in the storage unit 32 may be displayed on the display unit 34. Then, filtering parameters selected therefrom by user operation on the operation unit 33 are set as this-time filtering parameters. As also shown in FIG. 13, the number of times each set of filtering parameters has been selected (set) (the number of selected times) may also be displayed. This allows a user to readily set filtering parameters.

Alternatively, the filtering parameters may be set as follows: store in the storage unit 32 in advance correspondence tables for respective examinee background information (e.g., for respective ages, sexes, etc.), each of the corresponding tables storing therein imaging conditions correlated with the past records; and set, as this-time filtering parameters, values of filtering parameters which (i) are correlated, among the correspondence tables stored in the storage unit 32, in a correspondence table for the examinee background information contained in the supplementary information attached to the dynamic image, with the same imaging conditions as those contained in the supplementary information attached to the dynamic image, and (ii) are for the feature quantities set in Step S11. Alternatively, the filtering parameters may be set as follows: display, on the display unit 34, a correspondence table for the examinee background information (age, sex, etc.) contained in the supplementary information, the correspondence table being stored in the storage unit 32; and set filtering parameters selected therefrom by user operation on the operation unit 33 as this-time filtering parameters. That is, filtering parameter candidates to be displayed on the display unit 34 may be narrowed down by the examinee background information. If the examinee is a woman in her forties, only the correspondence table for women in their forties may be displayed on the display unit 34. This allows a user to select filtering parameters correlated with the same imaging conditions as those of the dynamic image to be filtered, taking into account the past records (the number of selected times) in a group of examinees having substantially the same background as the examinee, and accordingly can set filtering parameters with higher accuracy.

The filtering parameters for the feature quantity relating to time change (here, the time frequency) in pixel signal value of a dynamic image may be automatically set based on calculated feature quantities representing the dynamic state of structures contained in the dynamic image.

For example, because motion of the heart wall and pulmonary blood flow occur by heartbeat, it can be considered that motion frequency of the heart wall substantially matches the time frequency of the pulmonary blood flow signal component in a dynamic image. Further, because movement of the diaphragm, movement of the thorax and movement of the body-surface skin boundary face (boundary between the body (truck) and background) occur by respiration of the lungs (ventilation), it can be considered that motion frequency of the diaphragm, motion frequency of the thorax and motion frequency of the body-surface skin boundary face each substantially match the time frequency of a signal component of ventilation in a dynamic image. Further, because the main axis of the mediastinum moves by body movement, it can be considered that motion frequency of the main axis of the mediastinum substantially matches the time frequency of a signal component of body movement in a dynamic image.

Hence, in Step S12, the filtering parameters for the time frequency of pixel signal values of the dynamic image may be set, for example, as follows: analyze the dynamic image to obtain a motion cycle A of each of the heart wall, the diaphragm (or thorax or body-surface skin boundary face) and the main axis of the mediastinum; obtain a motion frequency f based on the obtained motion cycle A; and set the filtering parameters based on the obtained motion frequency f.

Figure 14:
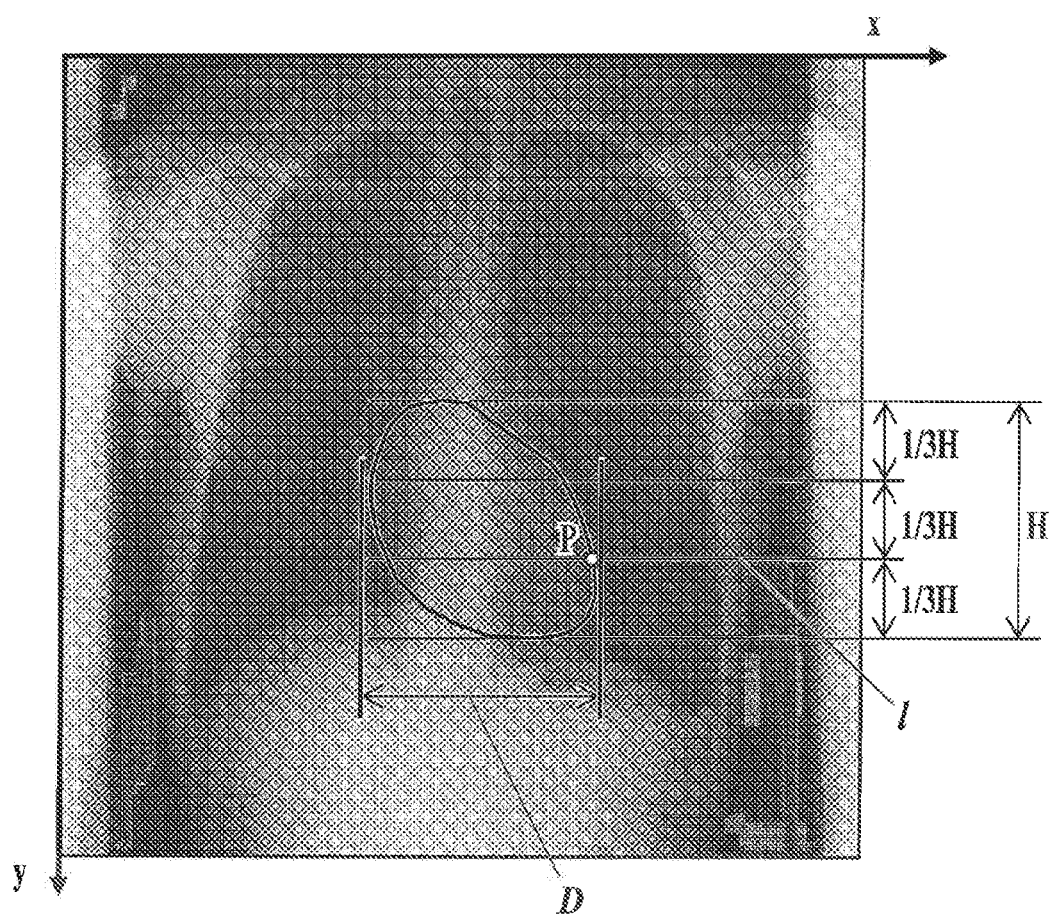
FIG. 14 is an illustration to explain a method for calculating motion frequency of the heart wall.

The motion frequency f of the heart wall can be obtained as follows. First, the heart contour is extracted from each frame image. The heart contour can be extracted by using well-known image processing techniques, such as a heart contour determination method described in Japanese Patent No. 279681. Next, as shown in FIG. 14, a reference point P is set on the left forth arch formed by the left ventricle. For example, the height H of the heart region defined by the extracted heart contour is divided into three equal parts, a horizontal line at one third of the height H from the bottom is taken as a measurement horizontal line 1, and a point of intersection of the measurement horizontal line 1 with the extracted heart contour in the left ventricle is taken as the reference point P. Then, the cycle $\lambda$ is obtained from difference in time between adjacent apexes in the waveform obtained by plotting x coordinates of the reference point p in a time sequence, and the motion frequency f of the heart wall is calculated by "frequency f=1/$\lambda$". Note that, in view of that the time frequency is grasped for observation of pulmonary blood flow, observation of the wall of the right ventricle, which pumps blood to the lungs, is actually preferred. However, since the motion cycle of the wall of the right ventricle is considered sufficiently approximate to that of the wall of the left ventricle, the contour of the wall of the left ventricle, which can be automatically obtained stably, is used for the calculation. The cycle $\lambda$ may be obtained from difference in time between adjacent apexes in the waveform obtained by plotting values of the diameter D of a transverse section of the heart region defined by the extracted heart contour in a time sequence. Then, the motion frequency f of the heart wall is calculated by "frequency f=1/$\lambda$".

Figure 15A:
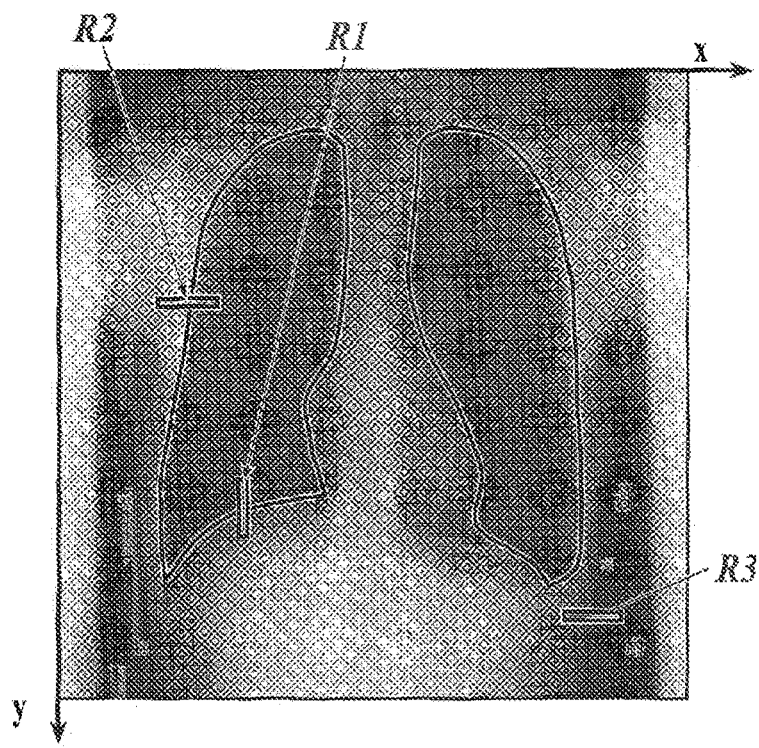
FIG. 15A is an illustration to explain an example of setting of regions of interest to calculate motion frequency of the diaphragm, motion frequency of the thorax and motion frequency of the body-surface skin boundary face.
Figure 15B:
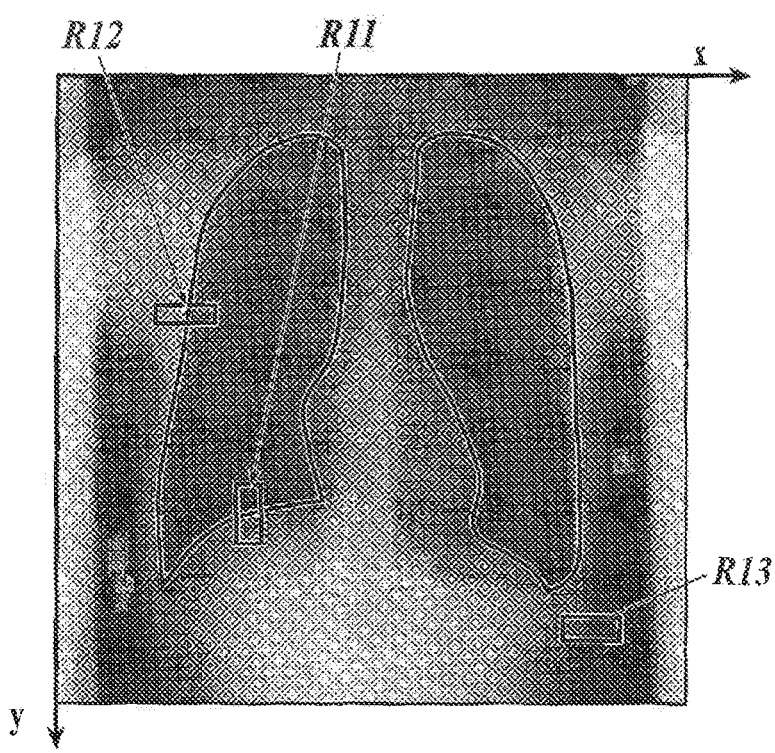
FIG. 15B is an illustration to explain another example of setting of regions of interest to calculate motion frequency of the diaphragm, motion frequency of the thorax and motion frequency of the body-surface skin boundary face.

The motion frequency f of the diaphragm can be obtained as follows. First, the diaphragm boundary is extracted from each frame image. The diaphragm boundary can be extracted by using well-known image processing techniques, such as a method based on iterative global threshold analysis and local threshold analysis described in Japanese Translation of PCT International Application Publication No. 2002-503861. After the diaphragm boundary is extracted, as shown in FIG. 15A, a region R1 is set at the position of a vertical cross section of the diaphragm boundary part, and the cycle $\lambda$ is obtained from difference in time between adjacent apexes in the waveform obtained by plotting values of a measure of central tendency (e.g., the mean, the median, etc.) of y coordinates of the diaphragm boundary in this region R1 in a time sequence. Alternatively, as shown in FIG. 15B, a region R11 may be set on the diaphragm boundary part, and the cycle λ is obtained from difference in time between adjacent apexes in the waveform obtained by plotting values of a measure of central tendency (e.g., the mean, the median, etc.) of pixel signal values in this region R11 in a time sequence. The motion frequency f of the diaphragm can be calculated by "frequency f=1/λ". When pixel signal values are utilized, it is unnecessary for the region R11 to be set to contain the diaphragm boundary in all the frame images, as long as the region R11 is set to be near the diaphragm boundary.

The motion frequency f of the thorax can be obtained as follows. First, the thorax boundary is extracted from each frame image. The thorax boundary can be extracted by using well-known image processing techniques, such as a method described in Japanese Translation of PCT International Application Publication No. 2002-503861. After the thorax boundary is extracted, as shown in FIG. 15A, a region R2 is set at the position of a horizontal cross section of the thorax boundary part, and the cycle λ is obtained from difference in time between adjacent apexes in the waveform obtained by plotting values of a measure of central tendency (e.g., the mean, the median, etc.) of x coordinates of the thorax boundary in this region R2 in a time sequence. Alternatively, as shown in FIG. 15B, a region R12 may be set on the thorax boundary part, and the cycle λ is obtained from difference in time between adjacent apexes in the waveform obtained by plotting values of a measure of central tendency (e.g., the mean, the median, etc.) of pixel signal values in this region R12 in a time sequence. The motion frequency f of the thorax can be calculated by "frequency f=1/λ".

The motion frequency f of the body-surface skin boundary face can be obtained as follows. First, the body-surface skin boundary face is extracted from each frame image. The body-surface skin boundary face can be extracted by using well-known image processing techniques, such as banalization. After the body-surface skin boundary face is extracted, as shown in FIG. 15A, a region R3 is set at the position of a horizontal cross section of the body-surface skin boundary face, and the cycle λ is obtained from difference in time between adjacent apexes in the waveform obtained by plotting values of a measure of central tendency (e.g., the mean, the median, etc.) of x coordinates of the body-surface skin boundary face in this region R3 in a time sequence. Alternatively, as shown in FIG. 15B, a region R13 may be set on the body-surface skin boundary face, and the cycle λ is obtained from difference in time between adjacent apexes in the waveform obtained by plotting values of a measure of central tendency (e.g., the mean, the median, etc.) of pixel signal values in this region R13 in a time sequence. The motion frequency f of the body-surface skin boundary face can be calculated by "frequency f=1/λ".

Figure 16:
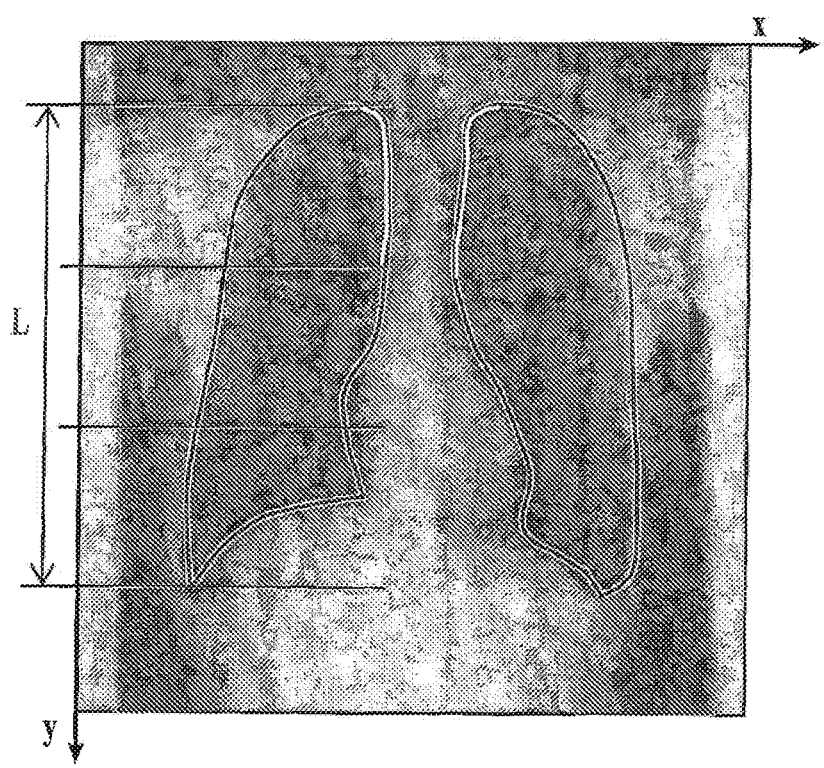
FIG. 16 is an illustration to explain a method for calculating motion frequency of the main axis of the mediastinum.

The motion frequency f of the main axis of the mediastinum can be obtained as follows. First, the lung regions are extracted from each frame image. The lung regions can be extracted by using well-known image processing techniques, such as a method described in Japanese Translation of PCT International Application Publication No. 2002-503861. After the lung regions are extracted, as shown in FIG. 16, first, in each of the contour lines of the right lung region and the left lung region, a line segment (white line(s) in FIG. 16) as a calculation target is determined. The line segment is determined, in x axis direction, in an area from one point having the minimum y coordinate (closest to the head) of the entire contour line to the midline, and in y axis direction, in an area of a desired length from the minimum y coordinate. The desired length is a length of a desired ratio (e.g., 1/3) of the length L (maximum y coordinate−minimum y coordinate) of the entire contour line in the y axis direction. Next, in the line segment as the calculation target, the position of the centroid of the line segment is calculated, and a time profile (a graph showing time change) of the position of the centroid is created. When a phenomenon is detected which has a track (locus) of the centroid moving away from a reference point in frame images a specific distance or more and also coming closer (moving back) to the reference point to be within the specific distance from the reference point, a period of time taken thereby is taken as the cycle λ of sway caused by body movement. The motion frequency f of the main axis of the mediastinum (frequency f of body movement) can be calculated by "frequency f=1/λ".

Alternatively, because a representative case of body movement is sway from side to side, instead of the centroid, a measure of central tendency (e.g., the mean, the median, the mode, etc.) of x coordinates of points of the line segment as the calculation target may be obtained. Then, a time profile (a graph showing time change) thereof is created. When a wave having an amplitude of a predetermined value or more is detected, a period of time taken by the wave (peak), i.e., peak time, is taken as the cycle λ of sway caused by body movement. The motion frequency f of the main axis of the mediastinum (body movement frequency f of body movement) can be calculated by "frequency f=1/λ".

If the analysis target is pulmonary blood flow, the filtering parameters for the time frequency are set to extract a range which contains the motion frequency f of the heart wall but does not contain the motion frequency f of the diaphragm (or thorax or body-surface skin boundary face) and the motion frequency f of the main axis of the mediastinum. Meanwhile, if the analysis target is ventilation, the filtering parameters for the time frequency are set to extract a range which contains the motion frequency f of the diaphragm (or thorax or body-surface skin boundary face) but does not contain the motion frequency f of the heart wall and the motion frequency f of the main axis of the mediastinum.

Alternatively, the filtering parameters for the feature quantity relating to time change in pixel signal value of a dynamic image may be automatically set based on the vital information detected by the vital sensor 15. If the vital sensor 15 is a pulse oximeter, arterial oxygen saturation (SpO$_2$) and/or pulse rate (PR) can be obtained as the vital information. Further, during inspiration, intrapleural pressure decreases and central venous pressure decreases, so that venous return increases, and this a little reduces the volume of the peripheral venous bed on which the pulse oximeter is mounted. Hence, the baseline of pulse waves to be detected by the pulse oximeter decreases. The opposite phenomenon occurs during expiration. Based on these, the respiratory rate can be estimated (Addison P S, et al., "Developing an algorithm for pulse oximetry derived respiratory rate (RRoxi): a healthy volunteer study.", Journal of Clinical Monitoring and Computing, 2012, 26(1), 45-51). Hence, the filtering parameters for the feature quantity relating to time change in pixel signal value of a dynamic image can be set as follows: obtain pulsation frequency and respiratory frequency by obtaining the inverses of the pulse rate and the respiratory rate, which are obtained from the vital sensor 15; and set the filtering parameters based on the obtained pulsation frequency and/or respiratory frequency.

A user can select (set), through the operation unit 33, a way of setting the filtering parameters from among the above-described ways.

When finishing setting the filtering parameters, the control unit 31 performs local matching and warping (nonlinear distortion transformation) on each frame image so as to align the frame images in terms of the lung field region (lung regions) (Step S13). For example, points (landmarks) as anatomical feature positions each shared by the frame images are extracted from each frame image, and a shift value of each landmark in each frame image from its corresponding landmark in a reference image is calculated. The frame image taken first is the reference image. Then, based on the calculated shift value of each landmark, a shift value of each of all pixels is calculated by approximation with $n^{th}$ polynomial, and frame images each composed of pixels each shifted by the calculated shift value are generated.

In this embodiment, imaging is performed during quiet breathing. During quiet breathing, position shift of the lung field region by respiration is a little. Hence, Step S13 may be skipped.

Next, the control unit 31 performs structure attenuation (Step S14). In Step S14, the control unit 31 attenuates, in each frame image, an image signal component(s) of a predetermined structure(s) unnecessary for analysis. Hereinafter, description is made about a case where the predetermined structure is ribs.

First, the ribs are extracted from each frame image. The ribs can be extracted by using well-known image processing techniques. Examples thereof include: template matching using prepared rib template(s); edge detection; and curve fitting (mathematical function fitting) after edge detection. Alternatively, as proposed in Japanese Patent Application Publication No. 2005-20338, used may be a method of projecting the shape(s) of the ribs initially detected by edge detection (shape detection with parabolic approximation) to a rib shape model (a rib shape generated as a linear sum of an average shape obtained from training data and principal component shapes obtained by principal component analysis of the training data), thereby obtaining a model projected shape of the ribs.

After the ribs are extracted from each frame image, a pixel value profile of rib region cross sections is created (by plotting signal pixel values on the vertical axis against positions in a frame image in the vertical direction on the horizontal axis) for each frame image. After a high spatial frequency component, such as noise, is removed by applying a low-pass filter to the created profiles, values of the pixel value profiles from which noise or the like has been removed are subtracted from the respective initial frame images. Thus, frame images with the image signal component of the ribs attenuated (ribs-attenuated frame images) can be obtained.

In this embodiment, the ribs are attenuated in the frame images, but the heart, the mediastinum, the diaphragm and/or the like may be attenuated. This structure attenuation may be performed after filtering in Step S15.

Next, the control unit 31 performs filtering on the dynamic image for noise removal in the set feature quantity space (here, the feature quantity space formed of two axes) with the filtering parameters set in Step S12 (Step S15). If the feature quantities set in Step S11 are a feature quantity relating to time change and a feature quantity relating to spatial change in pixel signal value of the dynamic image, the control unit 31 first performs filtering with the feature quantity relating to spatial change in pixel signal value of the dynamic image, and then performs filtering with the feature quantity relating to time change in pixel signal value of the dynamic image. For example, when the feature quantities set in Step S11 are the time frequency and the spatial frequency, the control unit 31 first performs, for each frame image, (i) Fourier transform, (ii) filtering with a bandpass filter, high-pass filter or low-pass filter based on the filtering parameters of the spatial frequency, and (iii) inverse Fourier transform. Alternatively, the control unit 31 may perform filtering with the spatial frequency by: dividing the lung field region of each of the frame images into small regions having a size according to the spatial frequency with the set filtering parameters; calculating, in each small region, a measure of central tendency (e.g., the mean, the median, etc.) of pixel signal values; and replacing the pixel signal values in the region with the calculated measure of central tendency. Next, the control unit 31 performs filtering with a high-pass filter, low-pass filter or bandpass filter in the time direction having cutoff frequencies corresponding to the filtering parameters of the time frequency, on time change in pixel signal value obtained by plotting, in the time direction, pixel signal values of corresponding pixels (or small regions) of the frame images (series of frame images) filtered with the spatial frequency. This can achieve noise removal in dynamic images with high accuracy.

Next, the control unit 31 stores in the storage unit 32 the filtering parameters of the respective feature quantities used in filtering (Step S16). For example, the control unit 31 correlates and stores in the storage unit 32 the filtering parameters of the respective feature quantities used in filtering with the supplementary information attached to the dynamic image which has just been filtered with the filtering parameters. If the table (correspondence table) in which imaging conditions (radiation emission conditions) are correlated with the actual results (past records) of filtering parameters set in the past is stored in the storage unit 32, the control unit 31 searches the correspondence table for a record having the imaging conditions and the filtering parameters of the feature quantities the same as those used this time. When retrieving such a record, the control unit 31 adds one to the number of selected times of the record (i.e., increments the number thereof by one). On the other hand, when not retrieving such a record, the control unit 31 adds a new record to the correspondence table, stores therein combination of the imaging conditions and the filtering parameters of the feature quantities used this time, and sets "1" in the number of selected times of the record.

Next, the control unit 31 divides the lung field region of the filtered frame images into small regions for analysis, and calculates, for each small region of the frame images, a feature quantity relating to the dynamic state of the lung field (Step S17). For example, the control unit 31 calculates, for each small region thereof, time change in measure of central tendency (e.g., the mean, the median, etc.) of pixel signal values, and calculates, based on this time change, one or more of the following (1) to (8) feature quantities as the feature quantity relating to the dynamic state of the lung field. Note that the small regions for analysis each may even be formed of one pixel.

(1) difference between the pixel signal values of the frame images which are adjacent to one another in terms of time;

(2) difference between the maximum pixel signal value and the minimum pixel signal value;

(3) difference between the minimum pixel value and each of the pixel signal values of the respective frame images;

(4) difference between the maximum pixel value and each of the pixel signal values of the respective frame images;

(5) peak integral calculated based on the profile shape of the pixel signal values in the time direction;

(6) peak distance calculated based on the profile shape of the pixel signal values in the time direction;

(7) speed ratio calculated based on the profile shape of the pixel signal values in the time direction; and (8) acceleration ratio calculated based on the profile shape of the pixel signal values in the time direction.

Next, the control unit 31 displays the feature quantity calculation result performed in Step S17 on the display unit 34 (Step S18), and then ends the image analysis process.

If the above (1), (3) or (4) is calculated in Step S17, the control unit 31 shows each small region of each frame image with brightness or in color according to the value of the feature quantity, and displays the frame images on the display unit 34 in the form of a video or to be apposed. If the above (2), (5), (6), (7) or (8) is calculated in Step S17, the control unit 31 shows each small region with brightness or in color according to the value of the feature quantity, and displays the same on the display unit 34. Alternatively, in Step S17, the control unit 31 may calculate, as the above-described feature quantity, a value which can be calculated for each cycle by any of the above Formulae 1 to 12 with the statistical marks (Σ, MAX, MED) excluded, show each small region in each cycle with brightness or in color according to the value of the feature quantity, and display images in the respective cycles on the display unit 34 in the form of a video.

As described above, according to the diagnostic console 3, the control unit 31 performs filtering on a dynamic image in a feature quantity space formed of two or more axes with feature quantities of the respective axes, the dynamic image being obtained by dynamic imaging performed by emitting radiation to an examination target site, and calculates a feature quantity relating to a dynamic state of the examination target site based on the filtered dynamic image. This can improve accuracy of noise removal in dynamic images.

For example, the control unit 31 sets a first parameter(s) for performing the filtering on the dynamic image in the feature quantity space formed of the two or more axes with the feature quantities of the respective axes, and performs the filtering on the dynamic image with the set first parameter(s).

Thus, filtering parameters for respective features of a feature quantity space formed of two or more axes are set for each dynamic image. This enables setting of filtering parameters for respective feature quantities according to individual difference, and hence can improve accuracy of noise removal in dynamic images. This effect is remarkably shown, in particular, in chest dynamic images taken during breathing because chest dynamic images taken during breathing have more noise than those taken during breath holding. Further, noise removal in dynamic images with high accuracy can prevent failure in analysis, which is performed after noise removal, and accordingly eliminate a need for redoing and improve work efficiency in medical settings, and also can improve accuracy of analysis.

Further, for example, the control unit 31 causes the display unit 34 to display a graph of the feature quantity space formed of the two or more axes, which is to be used in the filtering, and sets the first parameter(s), which is to be used in the filtering, based on user operation with respect to the displayed graph. This enables setting of filtering parameters for multiple feature quantities using GUI which user(s) can intuitively understand. Further, the display unit 34 displays, on the graph of the feature quantity space formed of the two or more axes, the guidance information G showing classification of signal components which can be contained in the dynamic image. This allows user(s) to intuitively understand meanings of feature quantities, and hence enables setting of filtering parameters with user(s) understood.

Further, for example, the control unit 31 obtains a second parameter(s) set in the past examination on the same examinee, and sets the first parameter(s), which is to be used in the filtering, based on the obtained second parameter(s). This enables setting of filtering parameters without user's effort.

Further, for example, the control unit 31 obtains, from the storage unit 32, a recommended parameter(s) correlated with the examinee background information which corresponds to the examinee background information attached to the dynamic image, and sets the first parameter(s), which is to be used in the filtering, based on the obtained recommended parameter(s). This enables ready setting of filtering parameters according to the feature(s), such as sex and/or age, of an examinee.

Further, the control unit 31 obtains, from the storage unit 32, the second parameter(s) correlated with the imaging condition(s) which substantially matches the imaging condition(s) of the dynamic image on which the filtering is to be performed, and sets the first parameter(s), which is to be used in the filtering, based on the obtained second parameter(s). This enables ready setting of filtering parameters according to imaging conditions.

Further, the control unit 31 analyzes the dynamic image, thereby obtaining a feature quantity representing a dynamic state of a predetermined structure contained in the dynamic image, and sets the first parameter(s) for, among the feature quantities, a feature quantity relating to time change in pixel signal value of the dynamic image based on the obtained feature quantity representing the dynamic state of the predetermined structure. This enables automatic setting of the optimum filtering parameters for a dynamic image without user's effort.

Further, the control unit 31 sets the first parameter(s) for the feature quantity relating to time change in pixel signal value of the dynamic image based on the vital information obtained from the vital sensor 15. This enables automatic setting of the optimum filtering parameters for the dynamic state of an examination target site of an examinee without user's effort.

Further, the control unit 31 performs the filtering on the dynamic image after attenuating an image signal component(s) of a specific structure(s) contained in the dynamic image. This can remove noise generated by structures from dynamic images in advance, and can further improve accuracy of noise removal in dynamic images.

Further, the control unit 31 displays the feature quantity relating to the dynamic state of the lung field, the feature quantity being calculated for each small region, on the display unit 34. This allows user(s) to grasp, for each small region, the feature quantity relating to the dynamic state of the lung field.

Those described in the above are preferred examples of the dynamic analysis system of the present invention, and not intended to limit the present invention.

For example, in the above, the chest is taken as an examination target site. However, other parts can also be taken as examination target sites.

Further, in the above, a hard disk, a nonvolatile semiconductor memory or the like is used as a computer readable medium of the programs of the present invention. However, this is not a limitation. As the computer readable medium, a portable storage medium such, as a CD-ROM, can be used. Further, as a medium to provide data of the programs of the present invention, a carrier wave can be used.

In addition to the above, detailed configurations and detailed actions of the devices or the like of the dynamic analysis system 100 can also be appropriately modified without departing from the spirit of the present invention.

What is claimed is:

1. A dynamic analysis device comprising a processor which:
performs filtering on a dynamic image in a feature quantity space formed of two or more axes with feature quantities of the respective axes, the dynamic image being obtained by dynamic imaging performed by emitting radiation to an examination target site; and
calculates a feature quantity relating to a dynamic state of the examination target site based on the filtered dynamic image,
wherein the feature quantities to be used in the filtering include at least one feature quantity relating to time change in pixel signal value of the dynamic image, which includes one or more of a time frequency of the pixel signal value of the dynamic image, and a feature quantity relating to a profile shape of the pixel signal value of the dynamic image in a time direction.

2. The dynamic analysis device according to claim 1, wherein the processor performs the filtering in the feature quantity space formed of the two or more axes having mutually different characteristics.

3. The dynamic analysis device according to claim 1, wherein the feature quantity relating to the profile shape of the pixel signal value of the dynamic image in the time direction is any of (i) a peak integral, (ii) a peak distance, (iii) a skewness, (iv) a speed ratio, and (v) an acceleration ratio, each of which is calculated based on the profile shape, and (vi) an output result obtained by inputting the profile shape to a machine learning classifier.

4. The dynamic analysis device according to claim 1, wherein the feature quantities to be used in the filtering further include at least one feature quantity relating to spatial change in the pixel signal value of the dynamic image.

5. The dynamic analysis device according to claim 4, wherein the feature quantity relating to the spatial change in the pixel signal value of the dynamic image is one or more of a spatial frequency of the pixel signal value of the dynamic image, and a curvature feature quantity representing a shape of a curved surface showing distribution of the pixel signal value in each frame image of the dynamic image.

6. The dynamic analysis device according to claim 1, wherein the processor sets a first parameter for performing the filtering on the dynamic image in the feature quantity space formed of the two or more axes with the feature quantities of the respective axes, and performs the filtering on the dynamic image with the set first parameter.

7. The dynamic analysis device according to claim 6, wherein the processor analyzes the dynamic image, thereby obtaining a feature quantity representing a dynamic state of a predetermined structure contained in the dynamic image, and sets the first parameter for, among the feature quantities, a feature quantity relating to time change in pixel signal value of the dynamic image based on the obtained feature quantity representing the dynamic state of the predetermined structure.

8. The dynamic analysis device according to claim 7, wherein the predetermined structure is one or more of a heart wall, a diaphragm, a thorax, a body-surface skin boundary face, and a mediastinum.

9. The dynamic analysis device according to claim 6, wherein the processor sets the first parameter for, among the feature quantities, a feature quantity relating to time change in pixel signal value of the dynamic image based on vital information on the examination target site obtained from a sensor which obtains not the dynamic image but the vital information.

10. The dynamic analysis device according to claim 6, further comprising a display unit which displays a graph of the feature quantity space formed of the two or more axes, wherein
the processor sets the first parameter based on a user operation with respect to the graph displayed by the display unit.

11. The dynamic analysis device according to claim 10, wherein the display unit displays, on the graph of the feature quantity space formed of the two or more axes, guidance information showing classification of signal components which can be contained in the dynamic image.

12. The dynamic analysis device according to claim 6, wherein the processor sets the first parameter by referring to a value of a second parameter set in a past examination.

13. The dynamic analysis device according to claim 12, wherein the processor obtains the second parameter set in the past examination on a same examinee, and sets the first parameter based on the obtained second parameter.

14. The dynamic analysis device according to claim 12, further comprising a storage unit in which an imaging condition is correlated and stored with the second parameter set for a past dynamic image taken under the imaging condition, wherein
the processor obtains, from the storage unit, the second parameter correlated with the imaging condition which substantially matches an imaging condition of the dynamic image on which the filtering is to be performed, and sets the first parameter based on the obtained second parameter.

15. The dynamic analysis device according to claim 6, further comprising a storage unit in which examinee background information is correlated and stored with a recommended parameter, wherein
the processor obtains, from the storage unit, the recommended parameter correlated with the examinee background information which corresponds to examinee background information attached to the dynamic image, and sets the first parameter based on the obtained recommended parameter.

16. The dynamic analysis device according to claim 1, wherein the processor divides each of frame images of the filtered dynamic image into small regions such that the small regions of the frame images correspond to one another, and calculates one or more of following (1) to (8) between the corresponding small regions of the frame images as the feature quantity relating to the dynamic state of the examination target site:
(1) a difference between pixel signal values of the frame images which are adjacent to one another in terms of time;
(2) a difference between a maximum pixel signal value and a minimum pixel signal value;
(3) a difference between the minimum pixel value and each of the pixel signal values of the respective frame images;

(4) a difference between the maximum pixel value and each of the pixel signal values of the respective frame images;
(5) a peak integral calculated based on a profile shape of a pixel signal value in a time direction;
(6) a peak distance calculated based on the profile shape of the pixel signal value in the time direction;
(7) a speed ratio calculated based on the profile shape of the pixel signal value in the time direction; and
(8) an acceleration ratio calculated based on the profile shape of the pixel signal value in the time direction.

17. The dynamic analysis device according to claim 1, further comprising a display unit which displays a calculation result of the feature quantity relating to the dynamic state of the examination target site.

18. The dynamic analysis device according to claim 1, wherein the processor attenuates an image signal component of a specific structure contained in the dynamic image.

19. A dynamic analysis system comprising:
an imaging device which performs dynamic imaging by emitting radiation to an examination target site, thereby obtaining a dynamic image; and
the dynamic analysis device according to claim 1.

20. A dynamic analysis device comprising a processor which:
performs first filtering on a dynamic image with a feature quantity relating to spatial change in pixel signal value of the dynamic image, the dynamic image being obtained by dynamic imaging performed by emitting radiation to an examination target site;
performs second filtering on the dynamic image with a feature quantity relating to time change in the pixel signal value of the dynamic image; and
calculates a feature quantity relating to a dynamic state of the examination target site based on the first-filtered and second-filtered dynamic image.

21. A dynamic analysis method comprising:
performing filtering on a dynamic image in a feature quantity space formed of two or more axes with feature quantities of the respective axes, the dynamic image being obtained by dynamic imaging performed by emitting radiation to an examination target site; and
calculating a feature quantity relating to a dynamic state of the examination target site based on the filtered dynamic image,
wherein the feature quantities to be used in the filtering include at least one feature quantity relating to time change in pixel signal value of the dynamic image, which includes one or more of a time frequency of the pixel signal value of the dynamic image, and a feature quantity relating to a profile shape of the pixel signal value of the dynamic image in a time direction.

22. A non-transitory computer readable storage medium storing a program for a computer to perform:
performing filtering on a dynamic image in a feature quantity space formed of two or more axes with feature quantities of the respective axes, the dynamic image being obtained by dynamic imaging performed by emitting radiation to an examination target site; and
calculating a feature quantity relating to a dynamic state of the examination target site based on the filtered dynamic image,
wherein the feature quantities to be used in the filtering include at least one feature quantity relating to time change in pixel signal value of the dynamic image, which includes one or more of a time frequency of the pixel signal value of the dynamic image, and a feature quantity relating to a profile shape of the pixel signal value of the dynamic image in a time direction.

* * * * *